(12) United States Patent
Rinehart et al.

(10) Patent No.: US 6,841,530 B2
(45) Date of Patent: Jan. 11, 2005

(54) SEMI-SYNTHETIC STUDIES TOWARD DIDEMNIN ANALOGUES

(75) Inventors: Kenneth L. Rinehart, Urbana, IL (US); Alexandra J. Katauskas, Lincoln, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 263 days.

(21) Appl. No.: 09/949,947

(22) Filed: Sep. 10, 2001

(65) Prior Publication Data

US 2002/0037835 A1 Mar. 28, 2002

Related U.S. Application Data

(63) Continuation of application No. 09/284,906, filed as application No. PCT/US97/19210 on Oct. 24, 1997.
(60) Provisional application No. 60/029,112, filed on Oct. 24, 1996.

(51) Int. Cl.[7] .......................... C07K 5/12; A61K 37/00
(52) U.S. Cl. ........................ 514/2; 514/10; 514/11; 514/183; 530/317; 540/455
(58) Field of Search ................. 514/2, 10, 11, 514/183; 530/317; 540/455

(56) References Cited

U.S. PATENT DOCUMENTS

| 4,493,796 A | 1/1985 | Rinehart .................. 260/112.5 |
| 4,948,791 A | 8/1990 | Rinehart et al. ............ 514/183 |
| 5,294,603 A | 3/1994 | Rinehart ...................... 514/10 |

*Primary Examiner*—Bennett Celsa
(74) *Attorney, Agent, or Firm*—Fish & Richardson P.C.

(57) ABSTRACT

Disclosed are semi-synthetic methods for the preparation of Didemnin Analogs. The compounds of this type are illustrated in Formula (I).

13 Claims, 29 Drawing Sheets

SEMI-SYNTHETIC STUDIES TOWARD DIDEMNIN ANALOGUES

CROSS REFERENCE TO RELATED APPLICATIONS

This application is a continuation of U.S. application Ser. No. 09/284,906, filed on Jul. 2, 1999, which is the National Stage of International Application No. PCT/US97/19210, filed on Oct. 24, 1997, which claims the benefit under 35 U.S.C. 119(e) of U.S. Provisional Application No. 60/029,112, filed on Oct. 24, 1996.

SUMMARY OF THE INVENTION

The syntheses of several didemnin derivatives, including didemnin M (1) as well as pyroglutaminyl didemnin B (2), have been performed. Didemnin M, one of the most active of the didemnins, contains pyroglutamate, glutamine, lactyl, and proline groups in its side chain, while pyroglutaminyl didemnin B contains only a pyroglutaminyl unit in addition to the lactyl and prolyl residues. Glutaminyl derivatives (3–5) were also synthesized in the process of producing didemnin M.

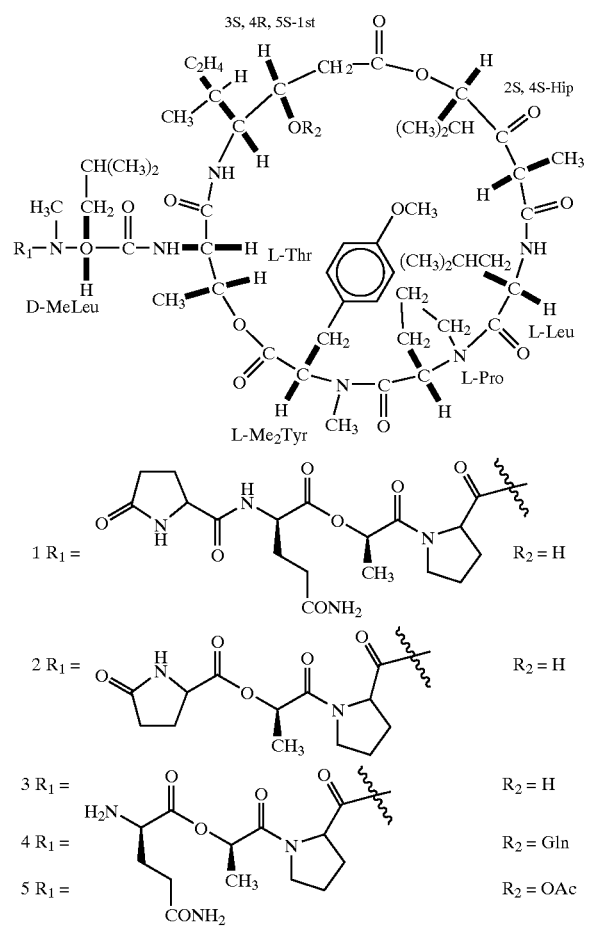

The retrosynthetic disconnections which formed the basis of a plan for preparation of the side chain of didemnin M are shown in Equation 1. Disconnection of the ester function between lactic acid and L-glutamine would give two units: a dipeptide, unit 7, comprised of pyroglutamate and glutamine; and unit 8, comprised of lactic acid and proline.

Equation 1

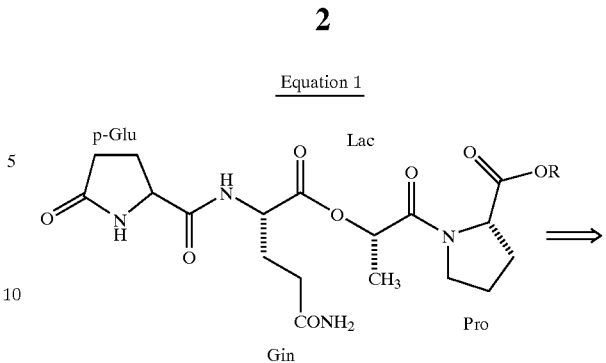

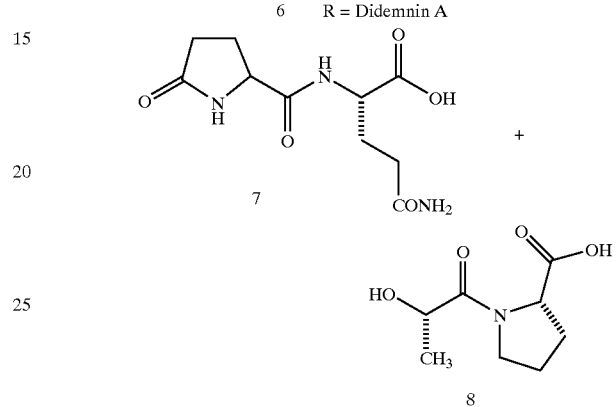

A mixed anhydride from L-pyroglutamic acid 9 and pivaloyl chloride was coupled with L-glutamine t-butyl ester 10 followed by acidic workup to yield L-pyroglutamyl-L-glutamine 7 (Equation 2). This dipeptide was purified by reversed phase HPLC using a gradient system of acetonitrile/H$_2$O.

Equation 2

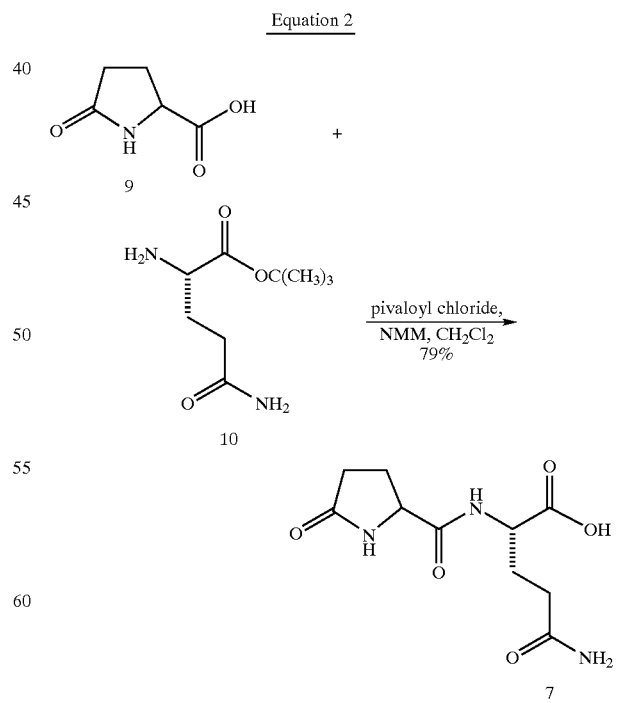

The synthesis of compound 8 began with protection of (S)-ethyl lactate, 11, as the benzyloxy derivative 12.

Hydrolysis provided the acid 13 which was coupled with L-proline phenacyl ester to afford compound 14. Treatment with a solution of zinc in acetic acid afforded 8 (Scheme I).

Scheme I

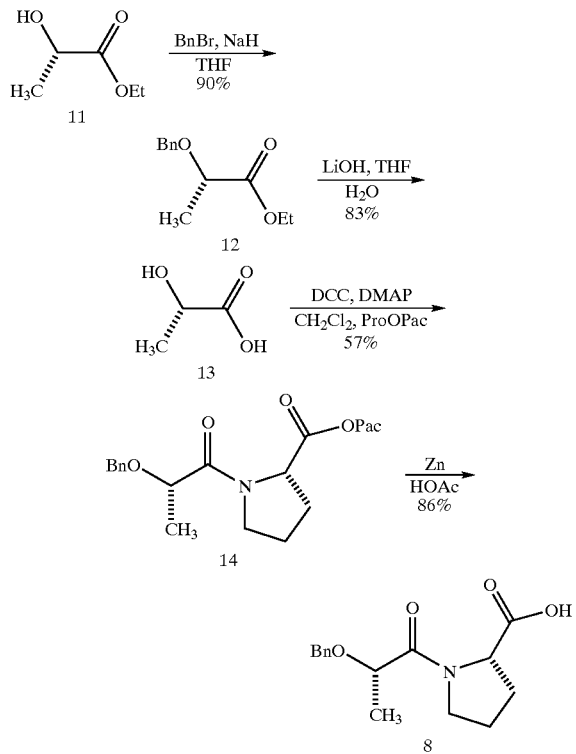

Didemnin M was synthesized by a three step scheme involving a coupling reaction of benzyllactylproline, 8, with didemnin A to give the protected derivative 15 followed by hydrogenation to yield didemnin B. The final step involved coupling of the pyroglutaminylglutamine unit, 7, with didemnin B. This was carried out using a variety of techniques with the most efficient being the mixed anhydride method (Scheme II). Purification was performed using HPLC with an acetonitrile/H₂O gradient system.

Scheme II

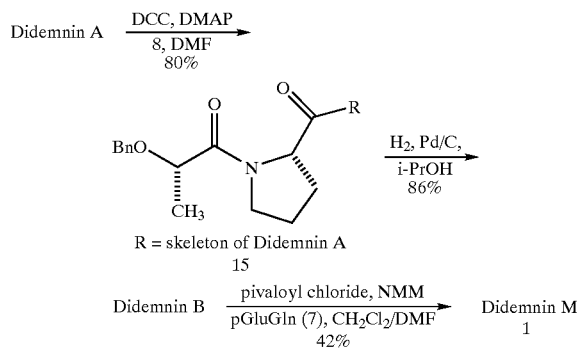

A second approach toward the synthesis of didemnin M involved protecting L-glutamine, 16, as the benzyloxycarbonyl derivative, 17, followed by coupling with didemnin B using DCC. During this coupling procedure, two glutaminyl derivatives were produced, 18, bore a glutaminyl residue at only the lactyl residue while the second, 19, contained two glutaminyl residues, one on the lactyl unit and the second on the isostatine unit. These derivatives were separated via reversed phase HPLC, then hydrogenated to provide the deprotected compounds 3 and 4 (Scheme III).

Scheme III

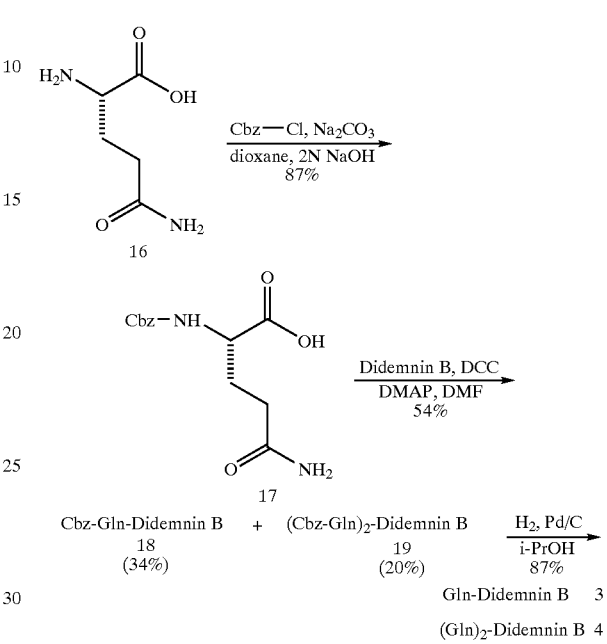

A different attempt at deprotection of the benzyloxycarbonyl derivative 18 provided yet another glutaminyl didemnin analogue. This analogue was formed upon treatment of 18 with hydrogen bromide in acetic acid. It appears as though an acetyl unit was added to the isostatine residue to provide compound 5 (Equation 3). These two compounds appear to be easily separable by reversed phase HPLC. This deprotection technique also proved to be useful with the dibenzyloxycarbonylglutaminyl derivative of didemnin B, 19.

Equation 3

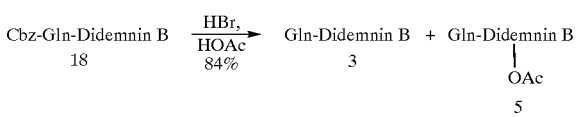

Pyroglutamic acid was protected as the benzyloxycarbonyl derivative (20) which was then coupled with glutaminyldidemnin B (3) using DCC to provide the protected form of didemnin M (21). Deprotection via hydrogenation afforded didemnin M (1) (Scheme IV). Purification via reversed phase HPLC provided the desired compound.

Scheme IV

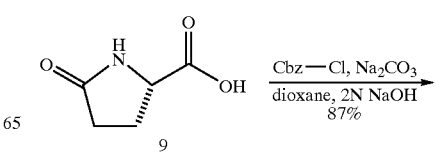

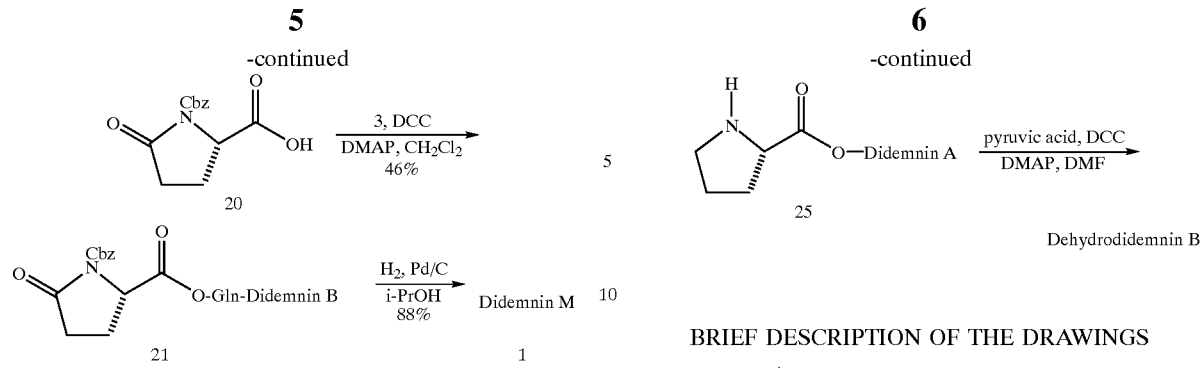

Another interesting analogue of didemnin is pyroglutaminyldidemnin B (2). The synthesis of 2 was accomplished by coupling 20 to didemnin B using EDC to provide Cbz-pyroglutaminyl didemnin B 22. Removal of the protecting group was accomplished using hydrogenation in the presence of a palladium catalyst to afford 2. Purification via reversed phase HPLC, using an acetonitrile/water gradient system, provided the pure compound (Equation 4).

Equation 4

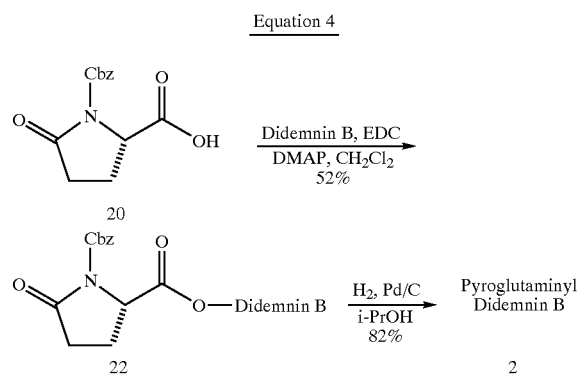

Dehydrodidemnin B was synthesized by first coupling Boc-L-proline (23) to didemnin A using EDC as the coupling agent. The Boc protecting group was removed upon treatment with acid and the resulting compound (25) was coupled with pyruvic acid to provide dehydrodidemnin B (Scheme V). The compound was purified via reversed phase HPLC using a gradient system of acetonitrile/H$_2$O.

Scheme V

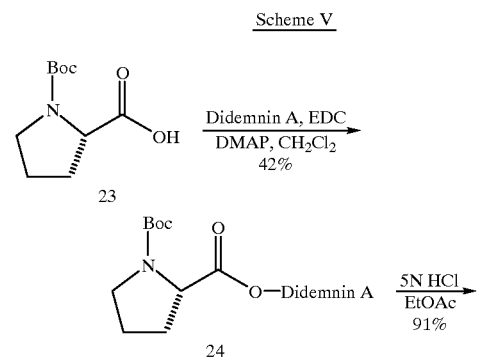

DETAILED DESCRIPTION OF THE PREFERRED EMBODIMENTS

Figure 1:
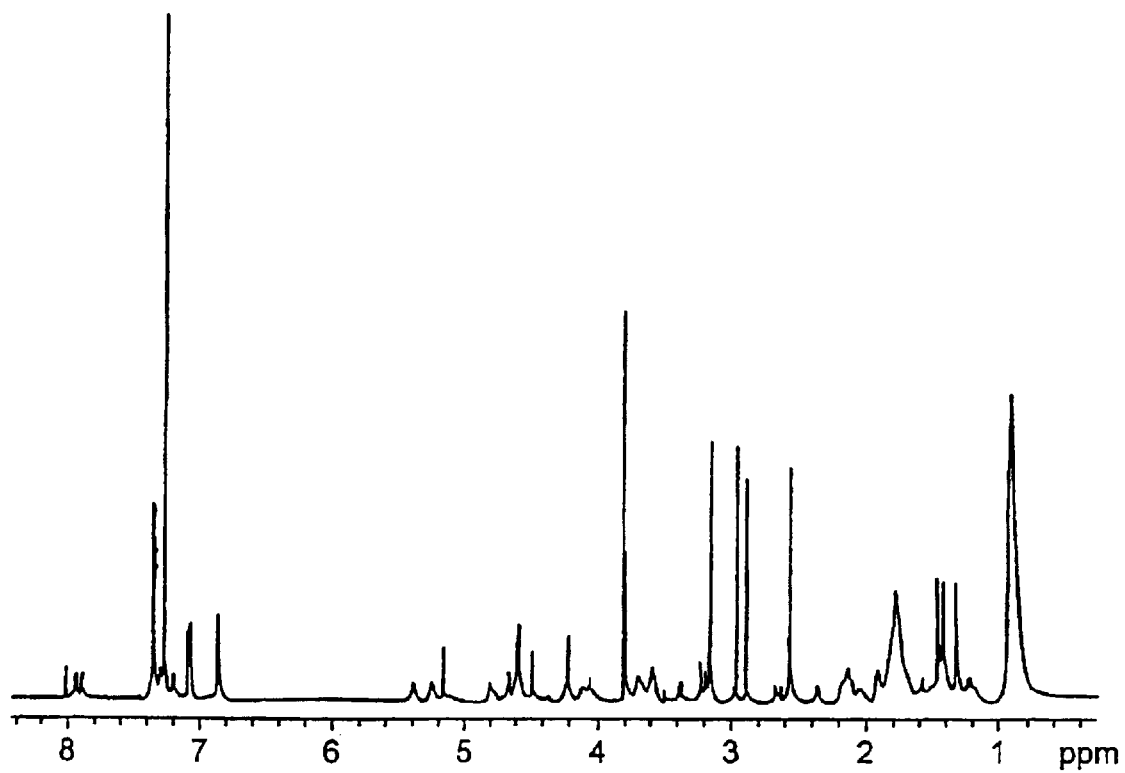
FIG. 1 is a $^1$H NMR spectrum of O-Benzyldidemnin B (15).
Figure 2:
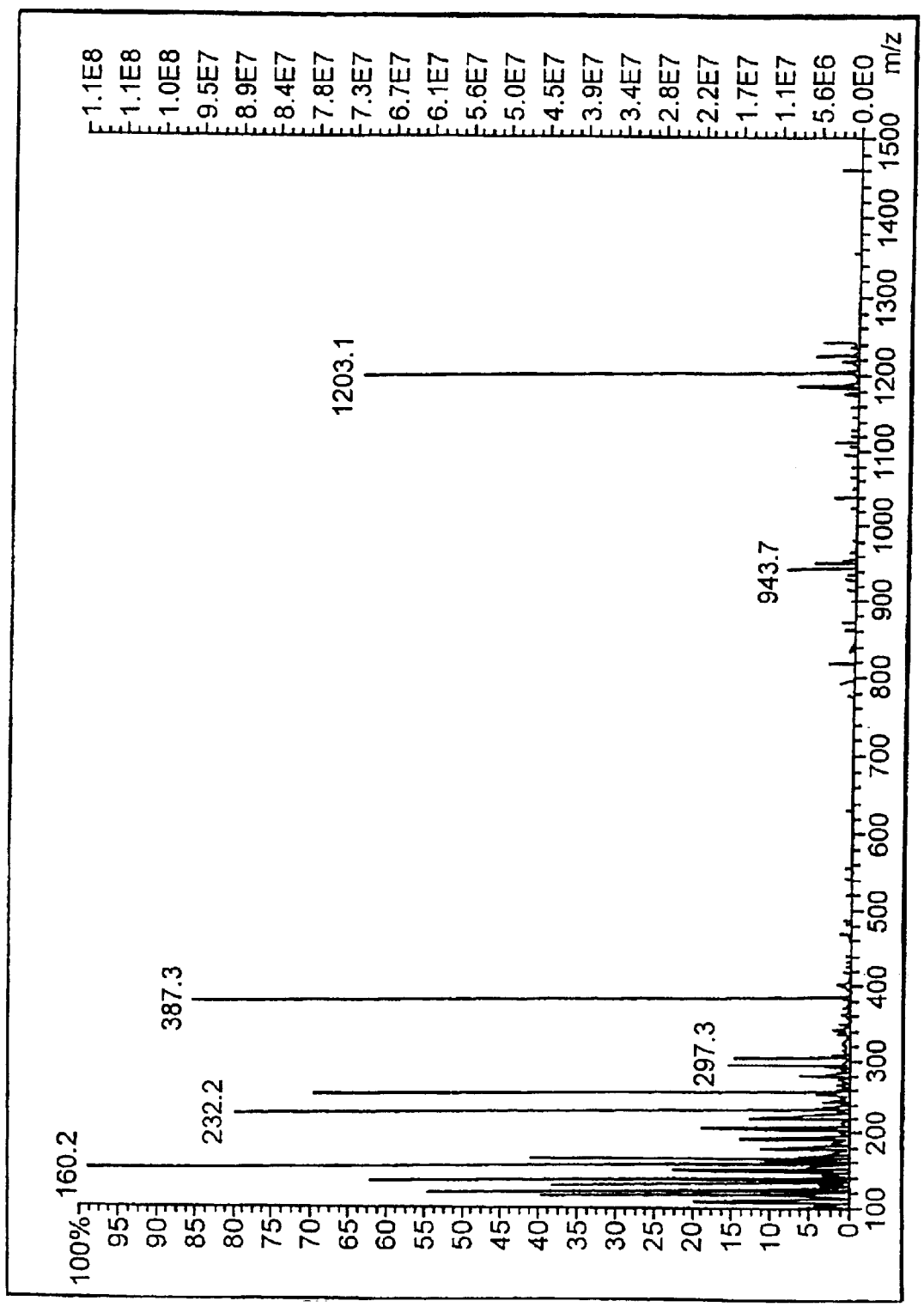
FIG. 2 is a LRFAB mass spectrum of O-Benzyldidemnin B (15).
Figure 3:
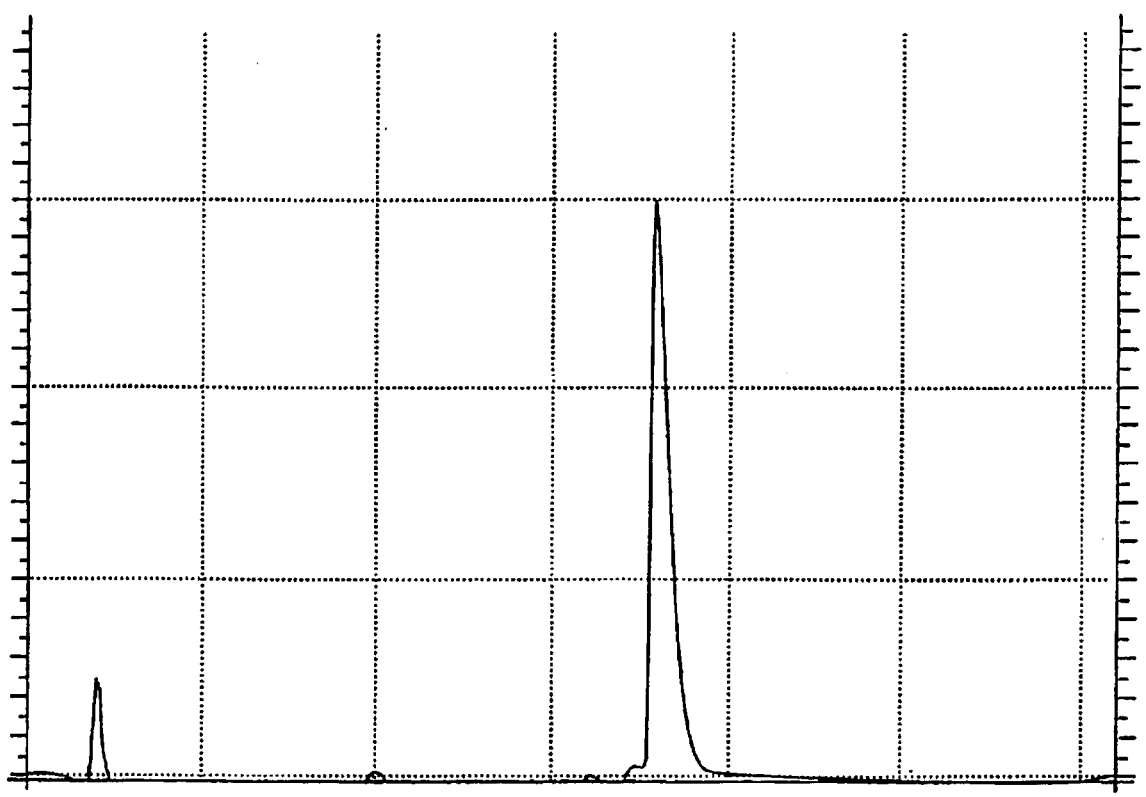
FIG. 3 is a RPHPLC trace of Didemnin B.
Figure 4:
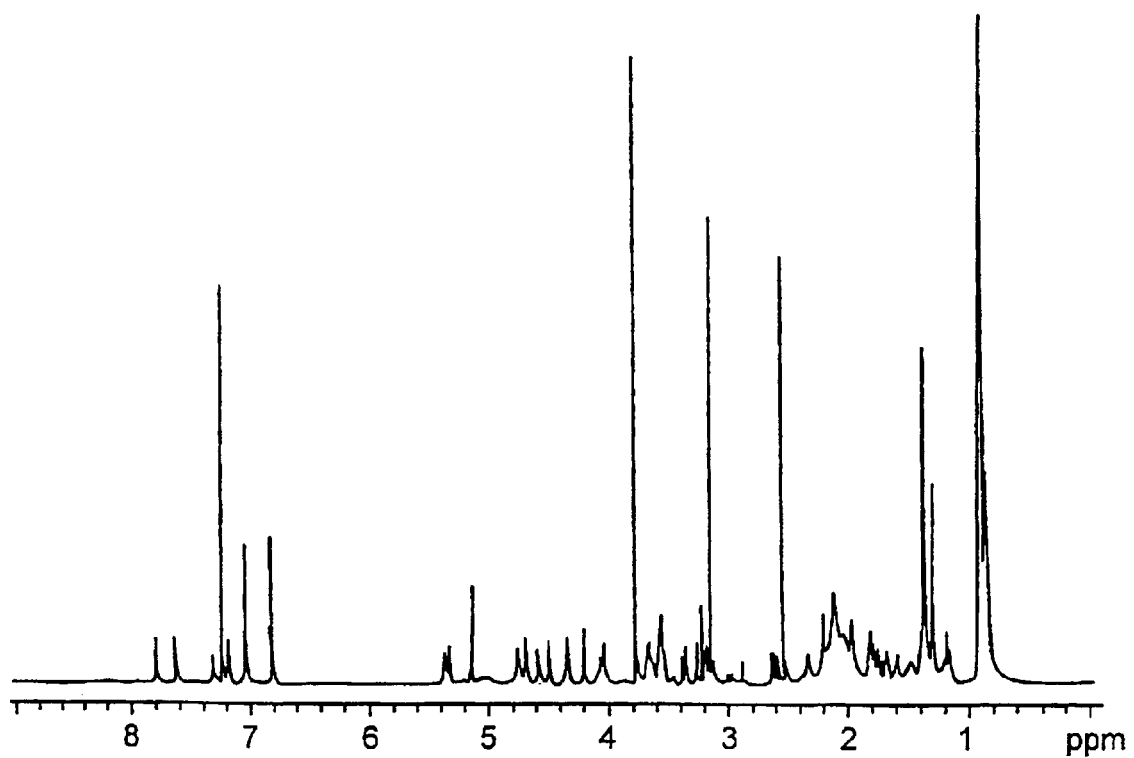
FIG. 4 is a $^1$H NMR spectrum of Didemnin B.
Figure 5:
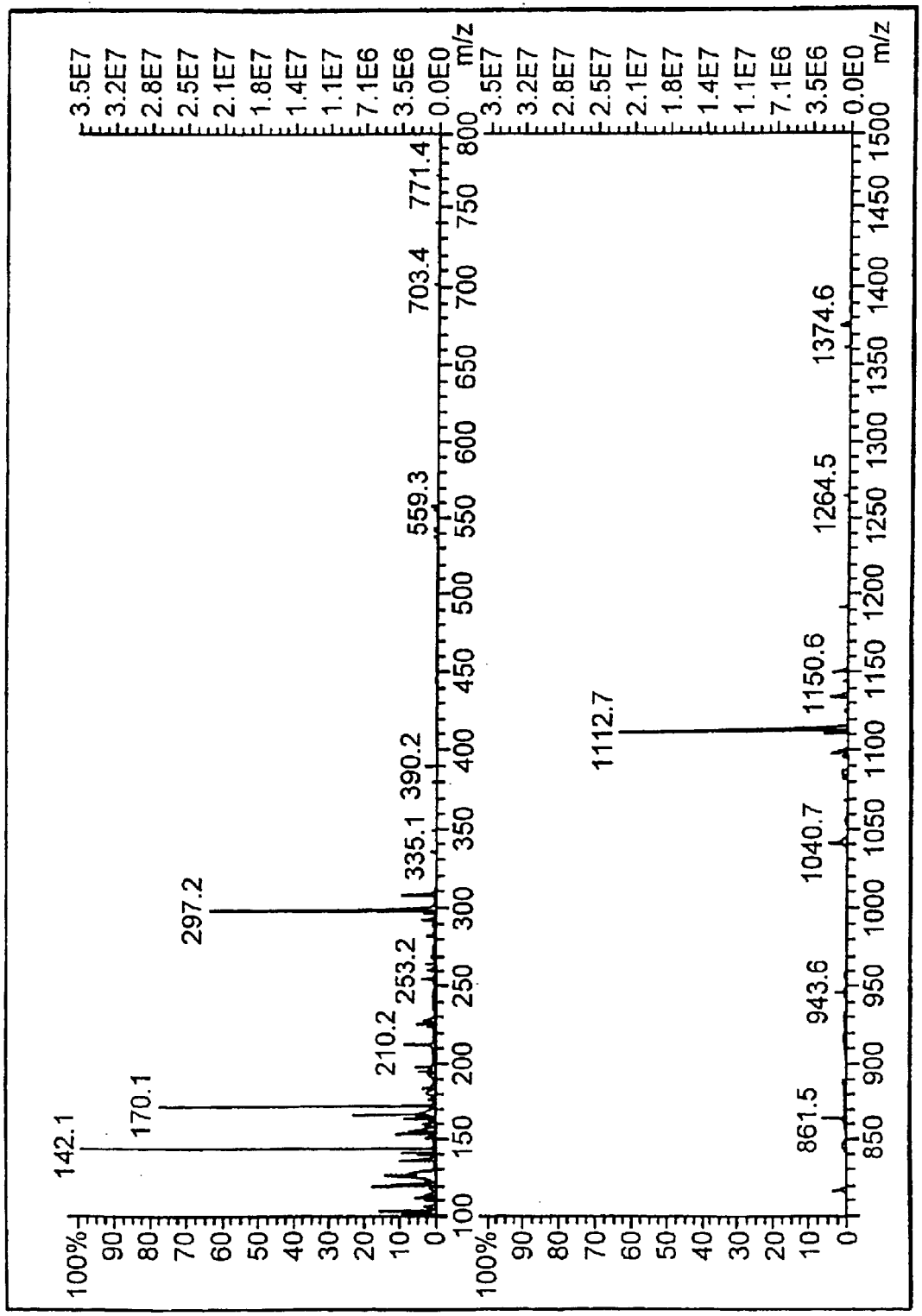
FIG. 5 is a LRFAB mass spectrum of O-Benzyldidemnin B (15).
Figure 6:
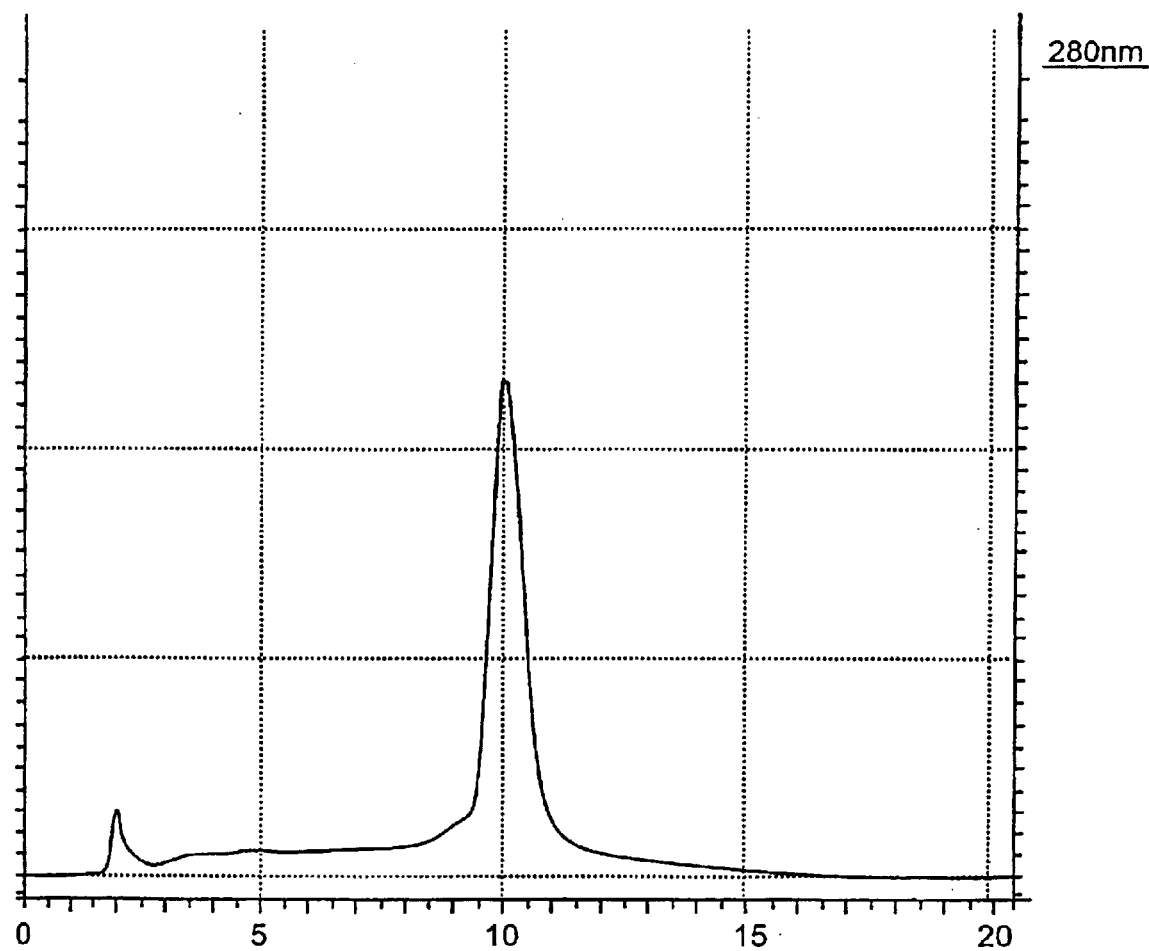
FIG. 6 is a RPHPLC trace of Didemnin M (1).
Figure 7:
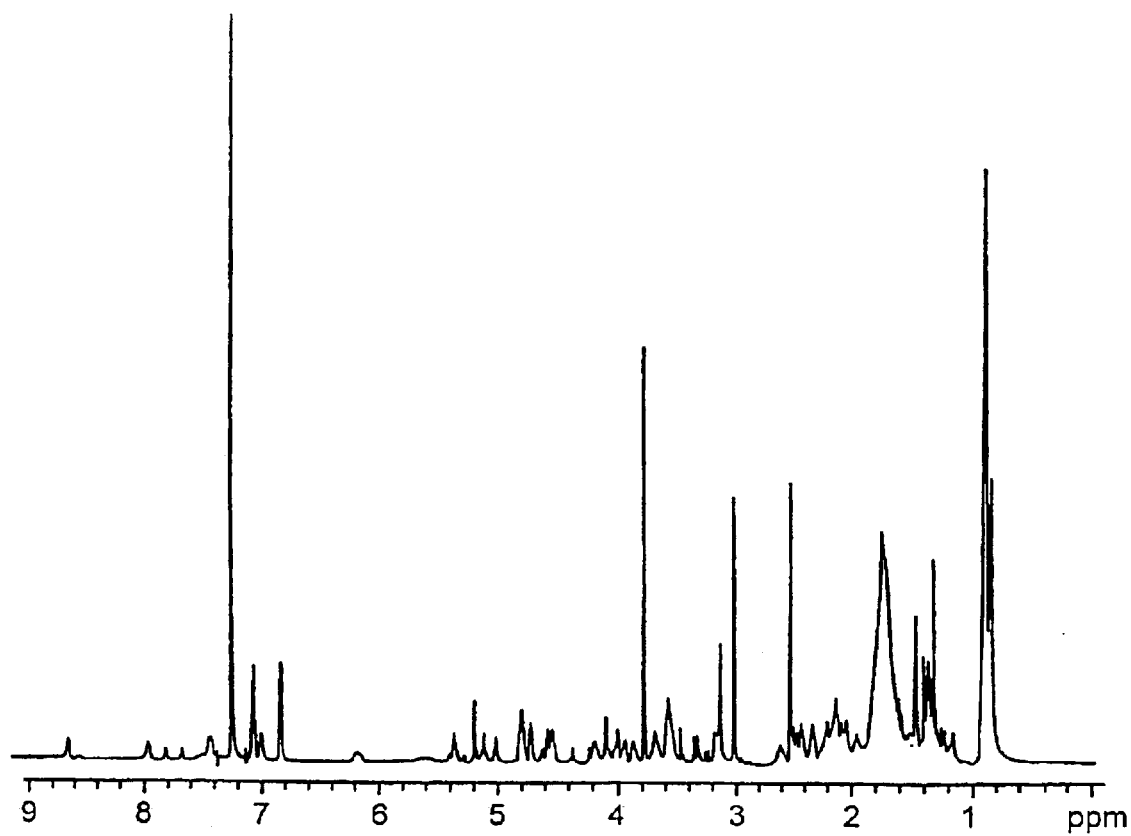
FIG. 7 is a $^1$H NMR spectrum of Didemnin M (1).
Figure 8:
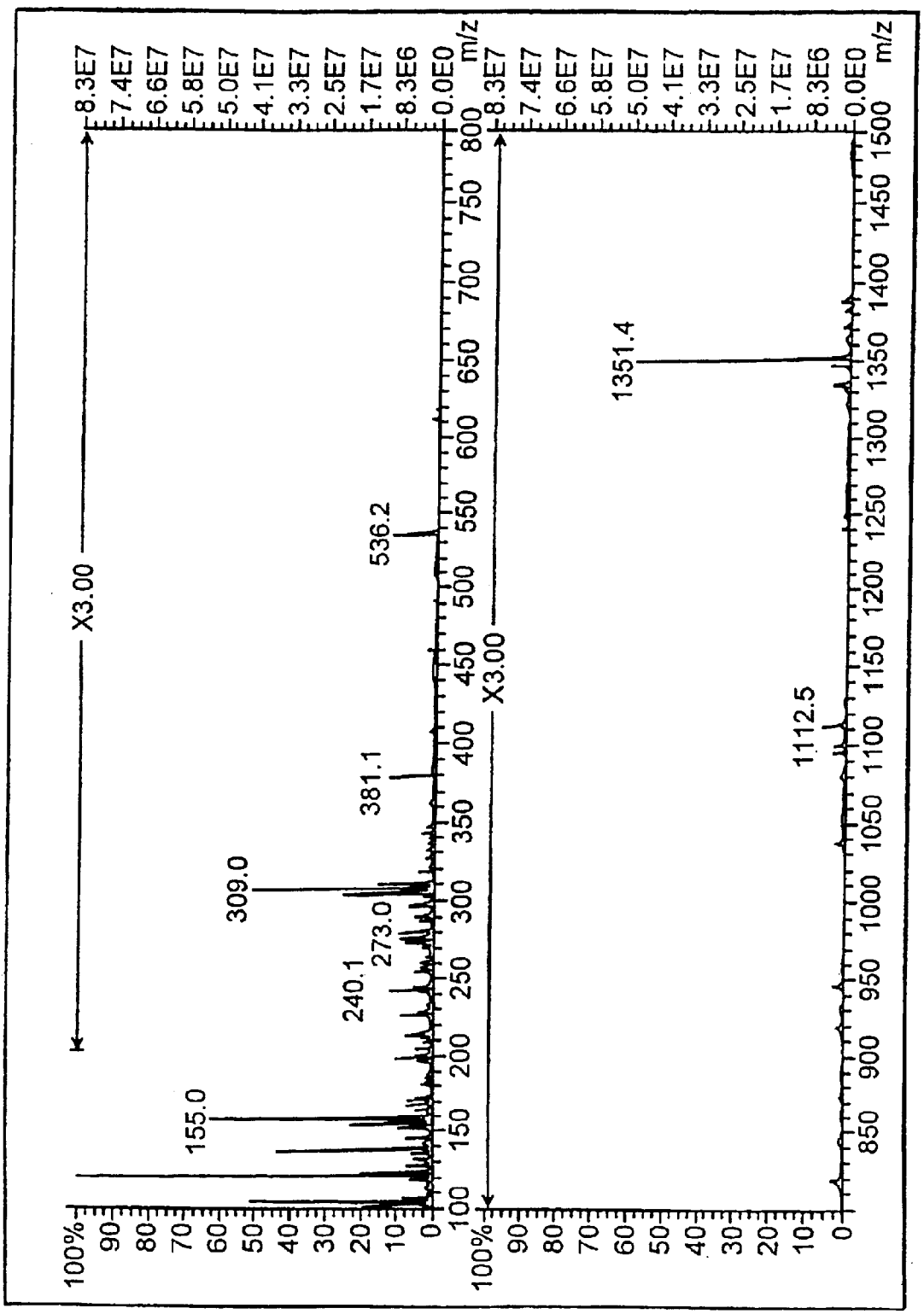
FIG. 8 is a LRFAB mass spectrum of Didemnin M (1).
Figure 9:
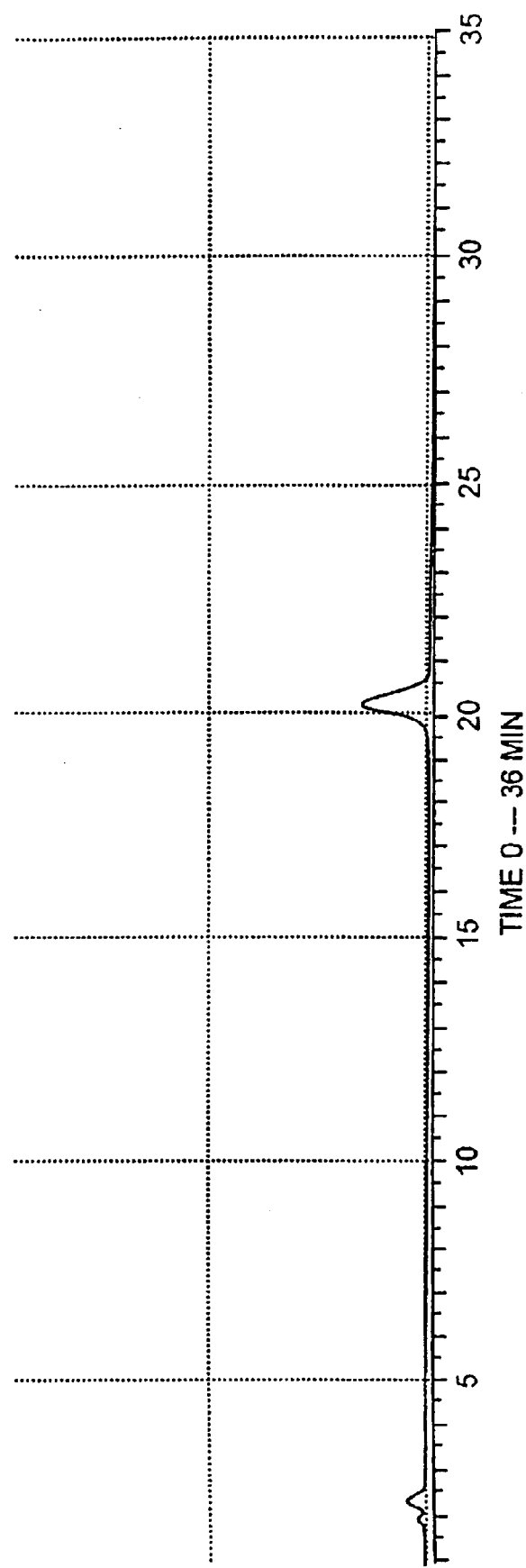
FIG. 9 is a RPHPLC trace of Benzyloxycarbonyl-L-Glutaminyldidemnin B (18).
Figure 10:
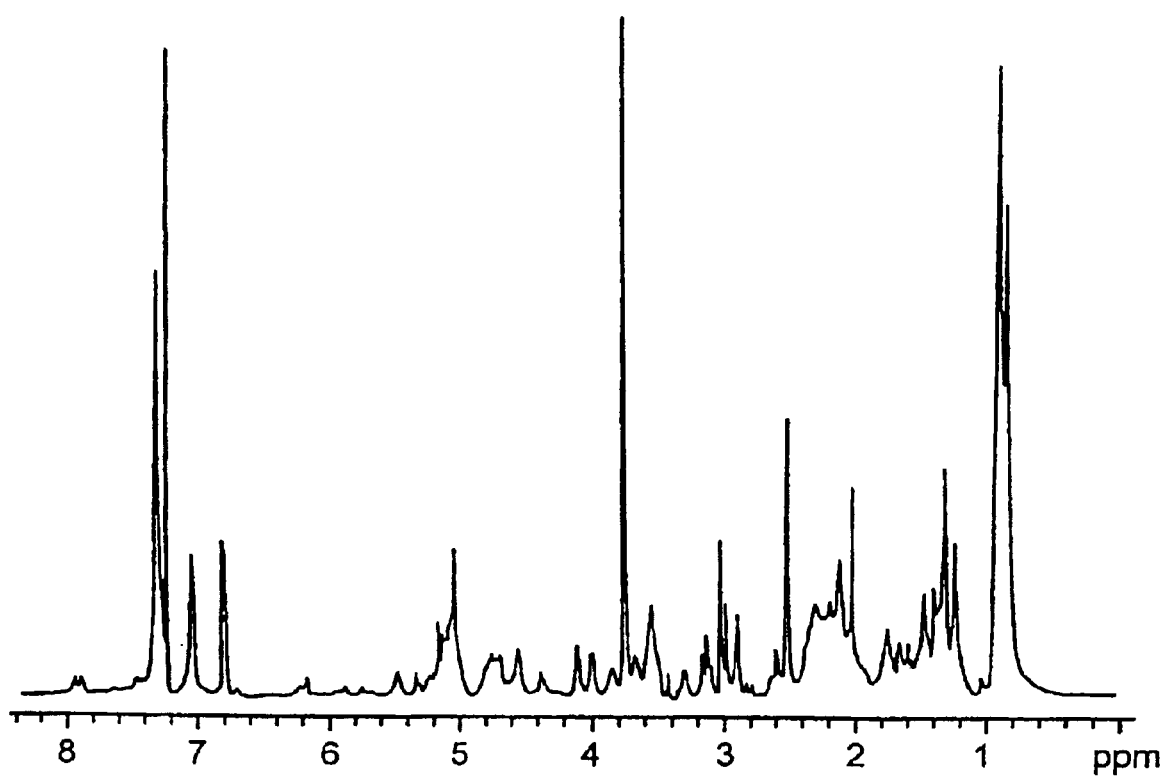
FIG. 10 is a $^1$H NMR spectrum of Benzyloxycarbonyl-L-Glutaminyldidemnin B (18).
Figure 11:
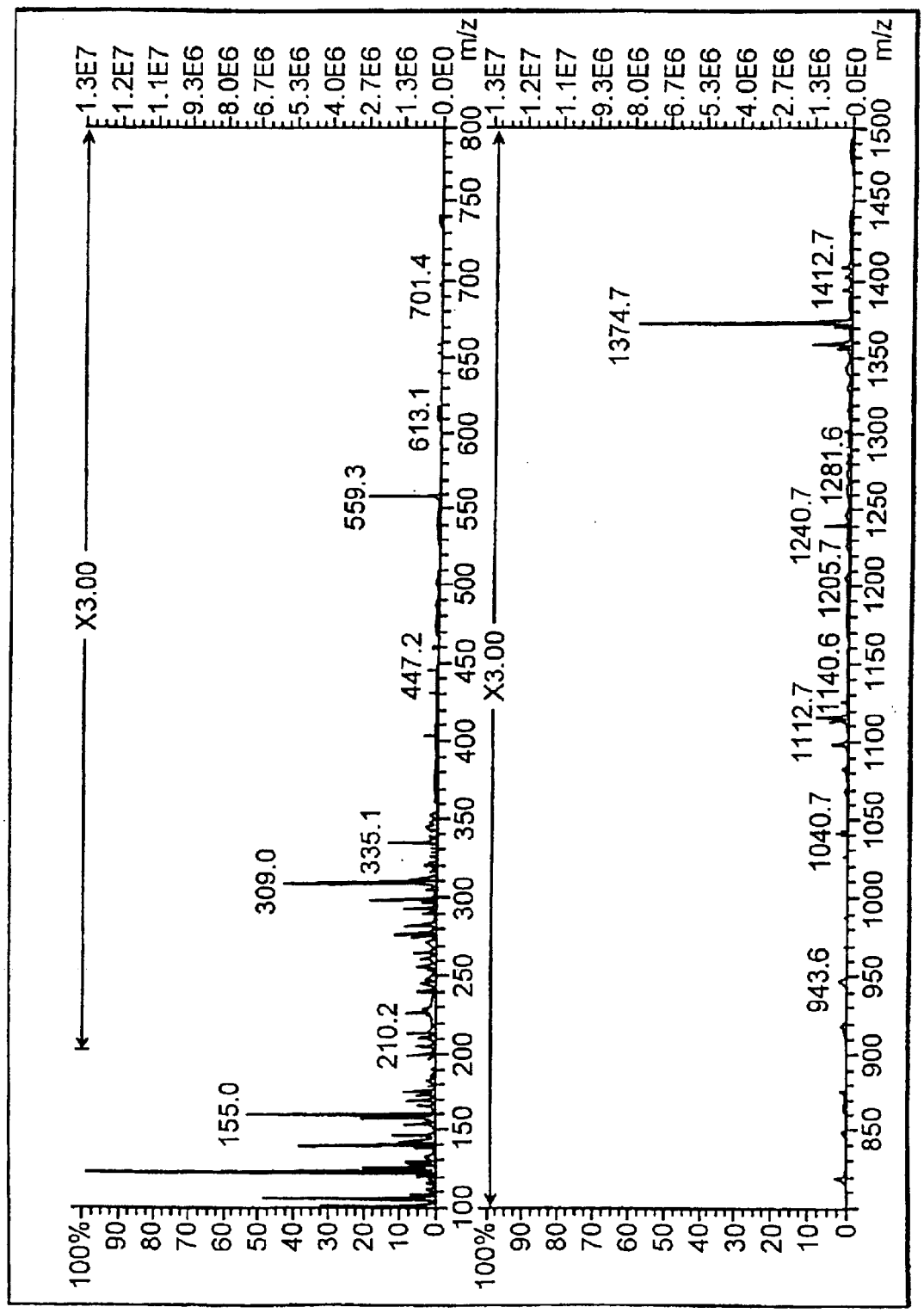
FIG. 11 is a LRFAB mass spectrum of Benzyloxycarbonyl-L-Glutaminyldidemnin B (18).
Figure 12:
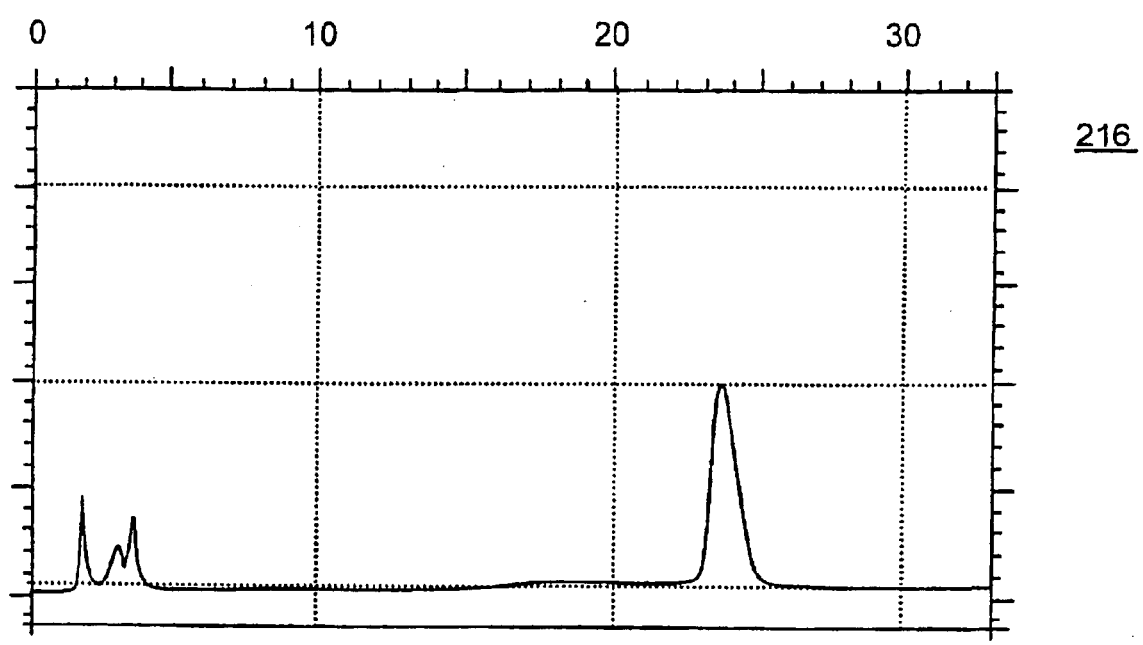
FIG. 12 is a RPHPLC trace of (Benzyloxycarbonyl-L-Glutaminy)$_2$.Didemnin M B(19).
Figure 13:
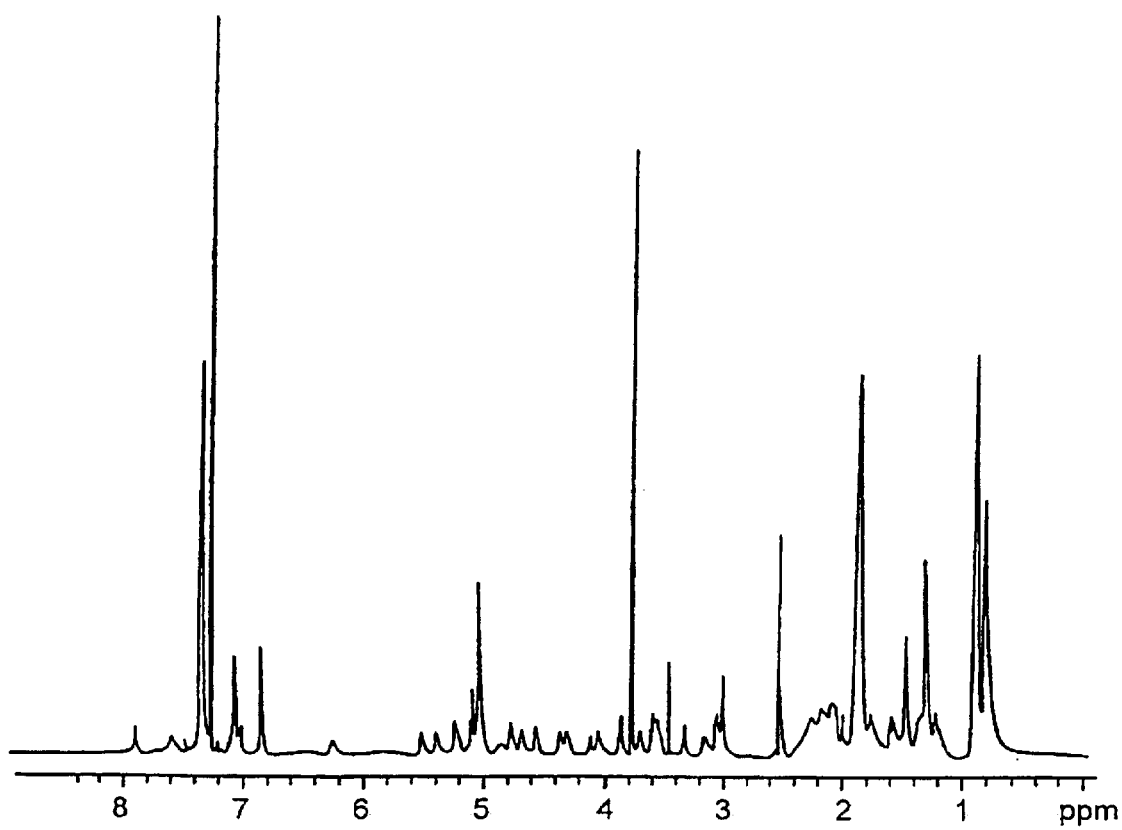
FIG. 13 is a $^1$H NMR spectrum of (Benzyloxycarbonyl-L-Glutaminy)$_2$.Didemnin M B(19).
Figure 14:
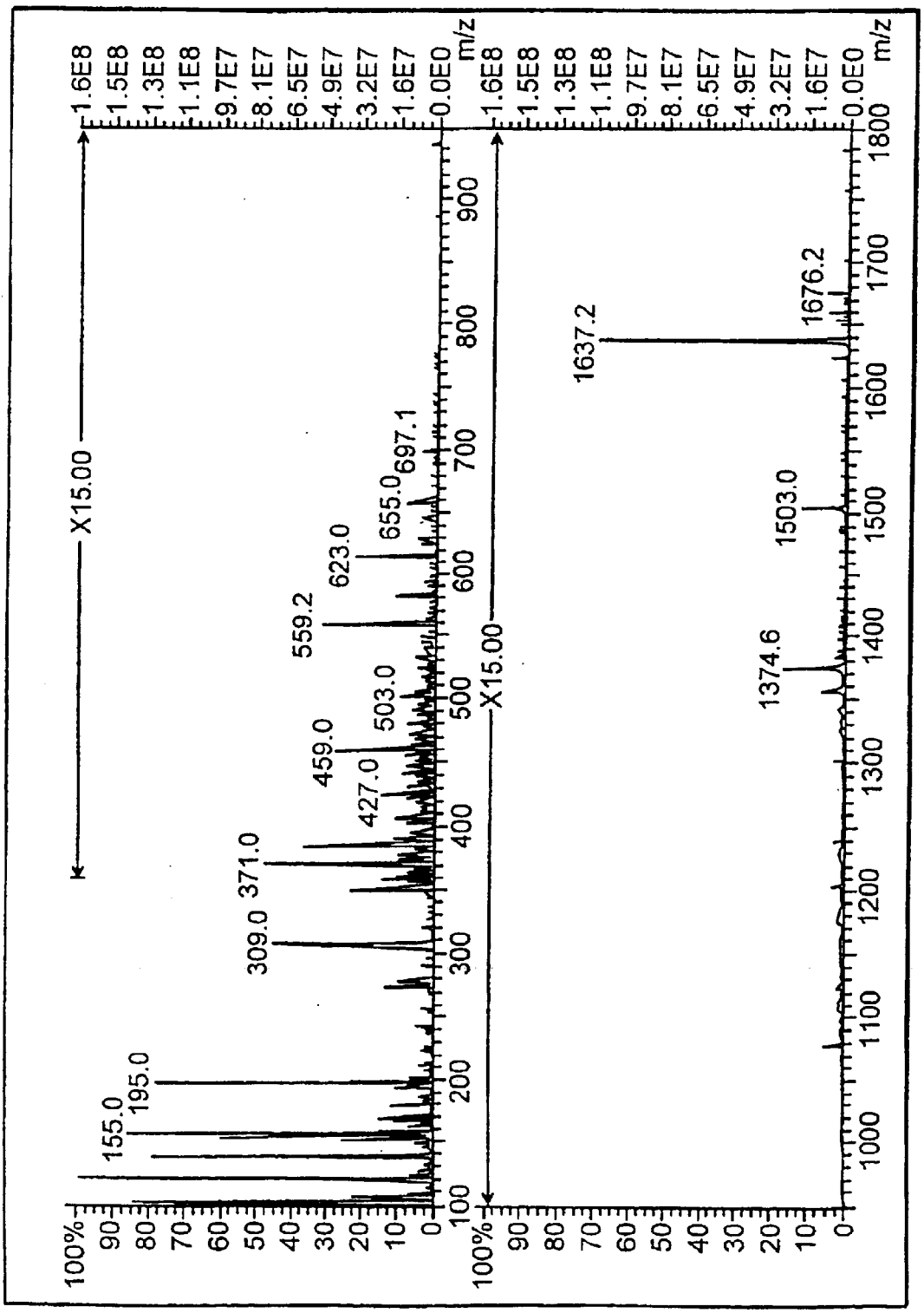
FIG. 14 is a LRFAB mass spectrum of (Benzyloxycarbonyl-L-Glutaminy)$_2$.Didemnin M B(19).
Figure 15:
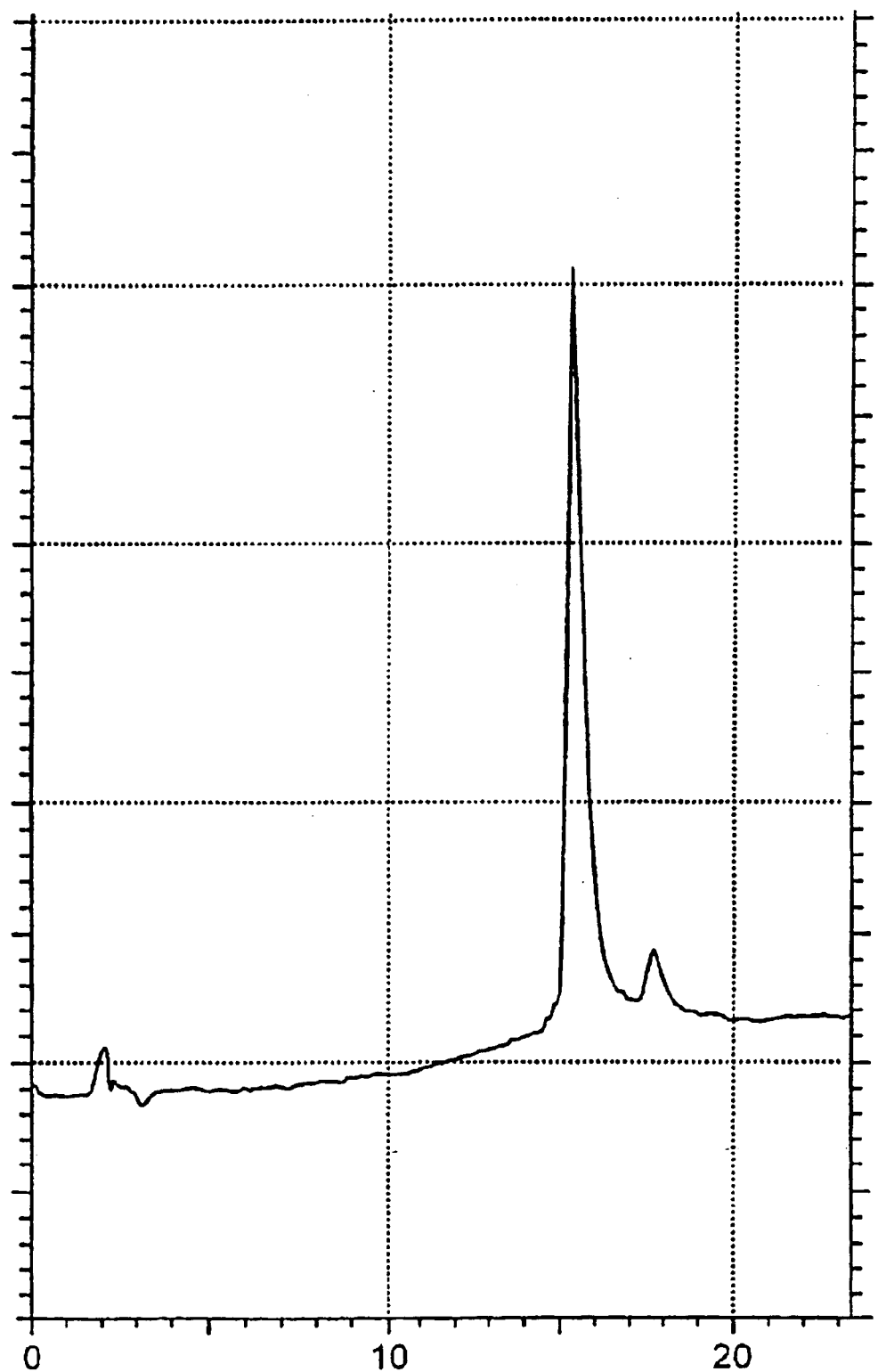
FIG. 15 is a RPHPLC trace of Glutaminyldidemnin B (3).
Figure 16:
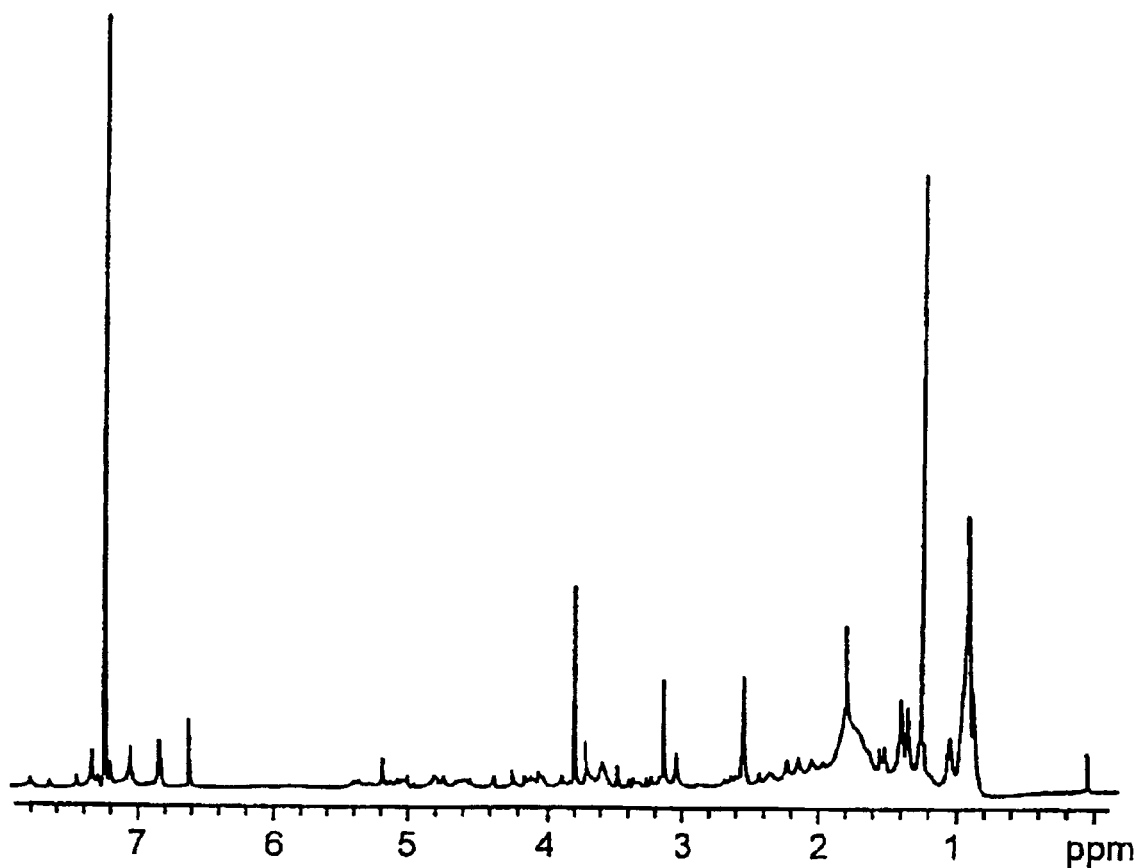
FIG. 16 is a $^1$H NMR spectrum of Glutaminyldidemnin B (3).
Figure 17:
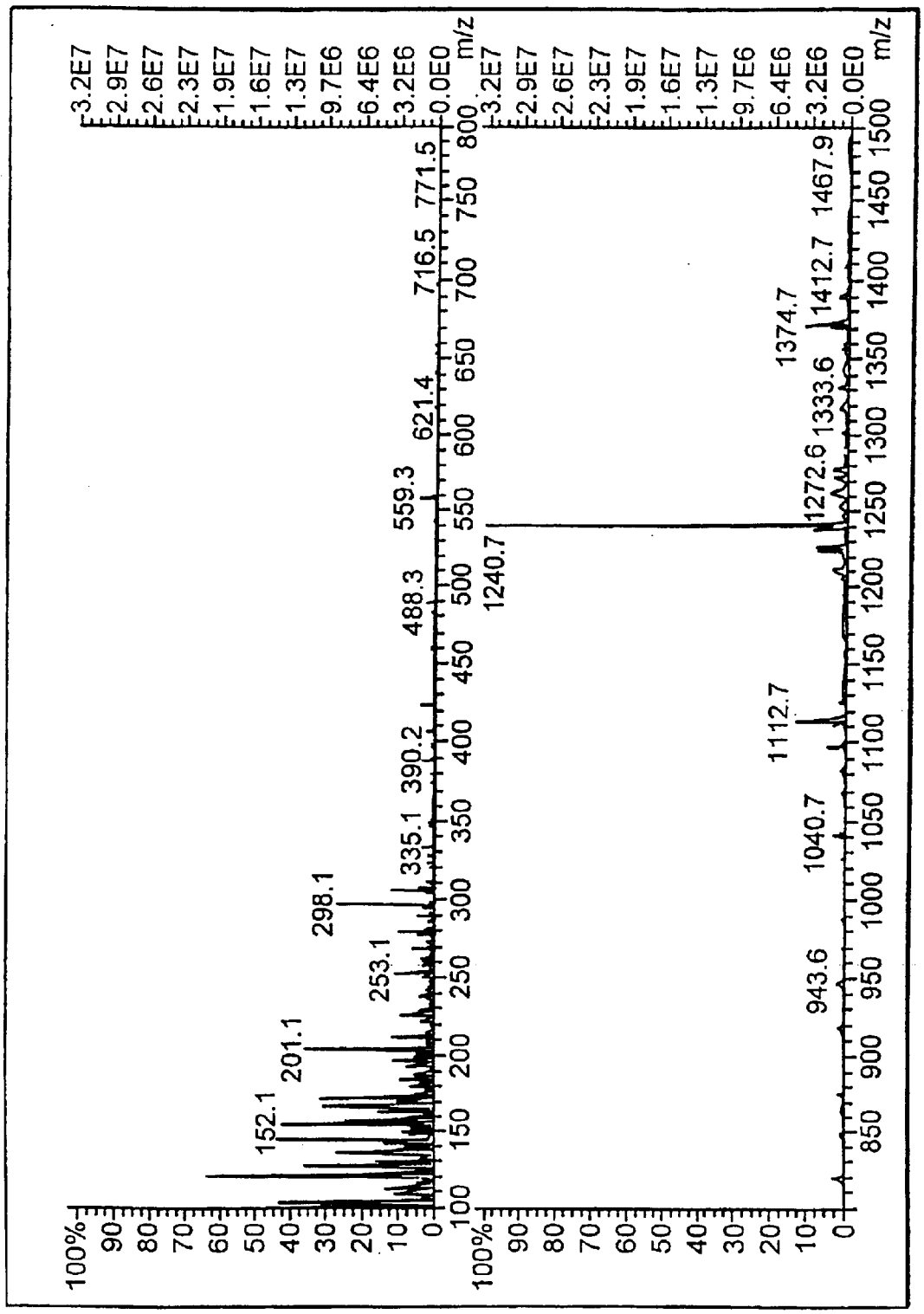
FIG. 17 is a LRFAB mass spectrum of Glutaminyldidemnin B (3).
Figure 18:
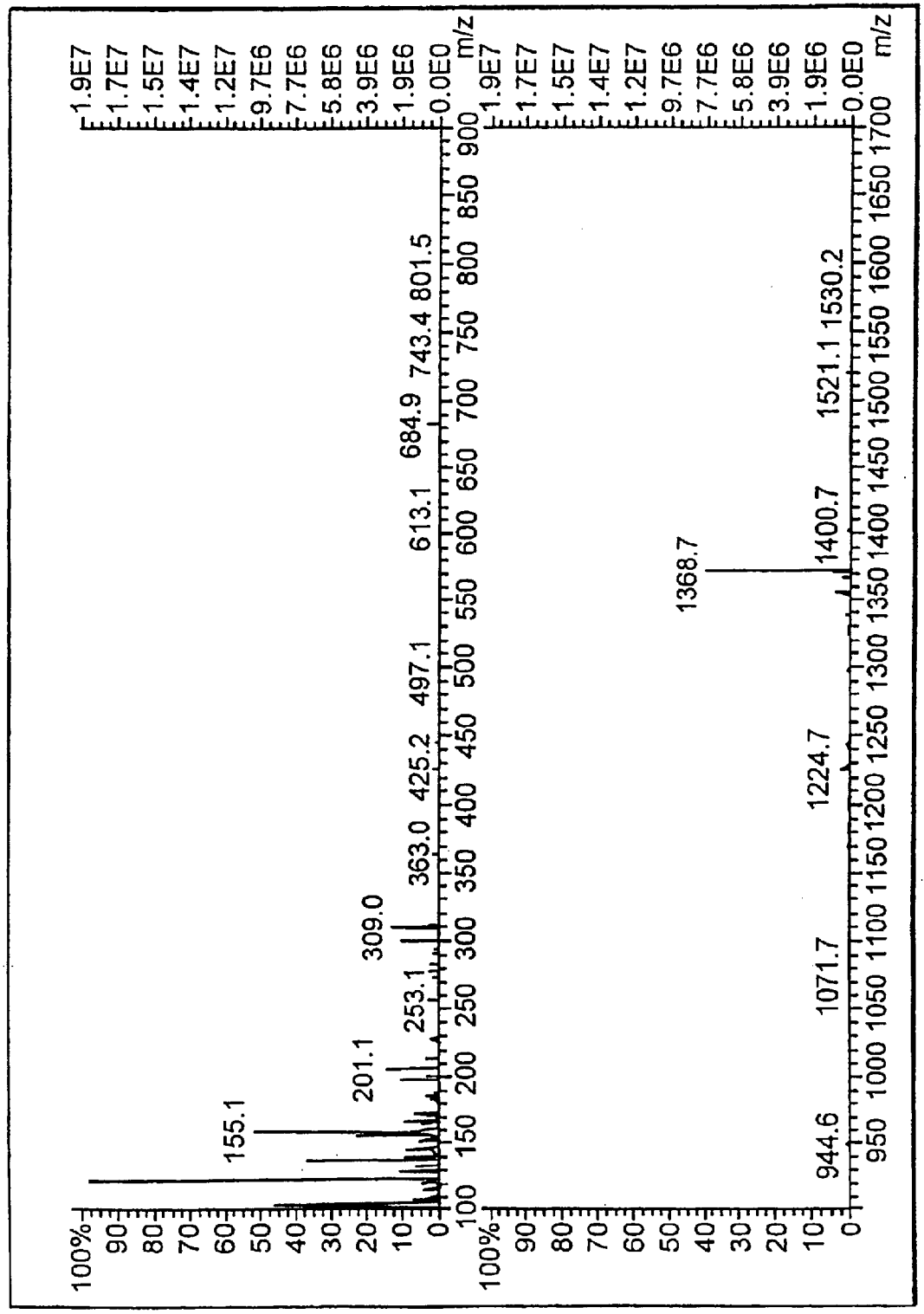
FIG. 18 is a LRFAB mass spectrum of Diglutaminyldidemnin B (4).
Figure 19:
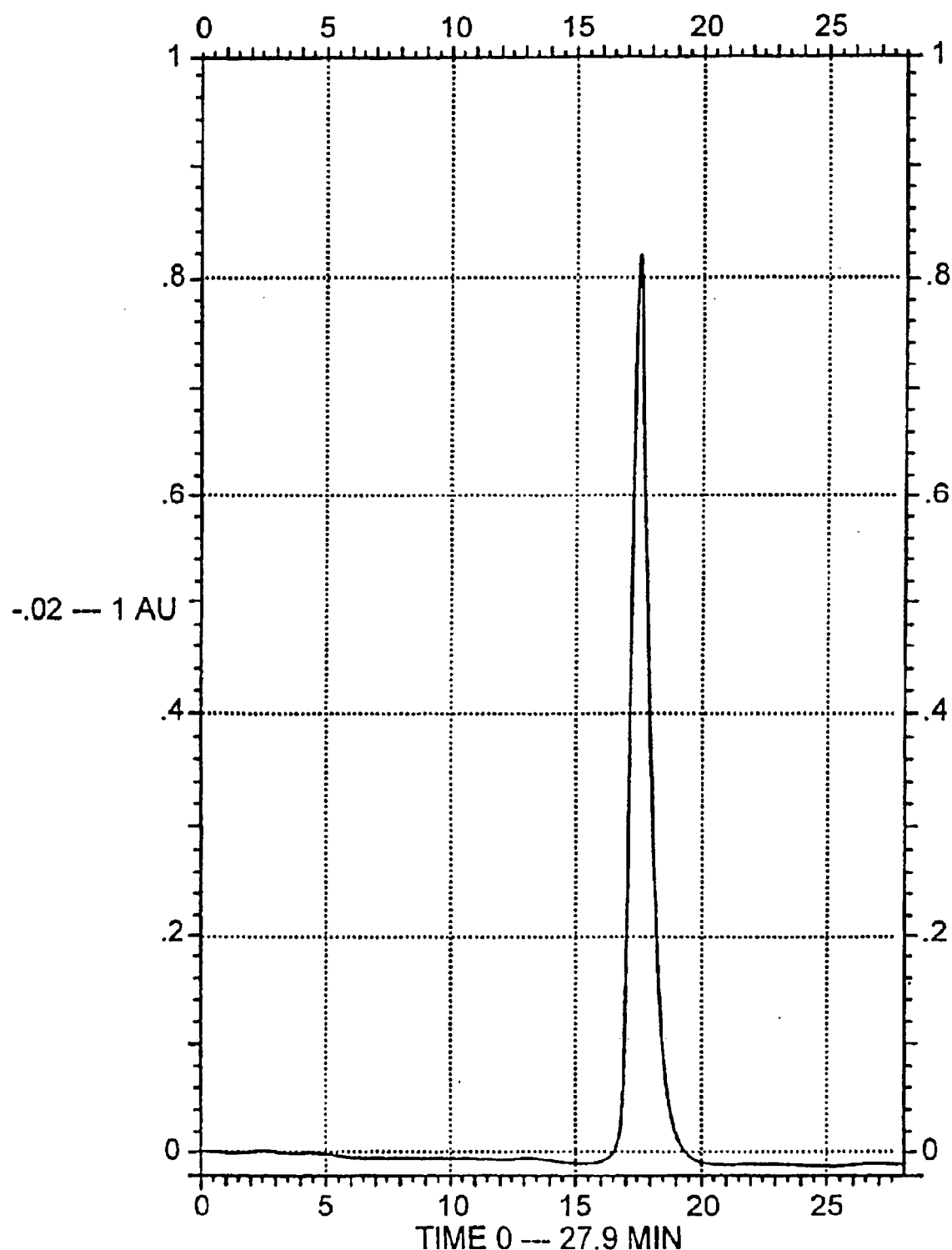
FIG. 19 is a RPHPLC trace of Benzyloxycarbonyldidemnin M (21).
Figure 20:
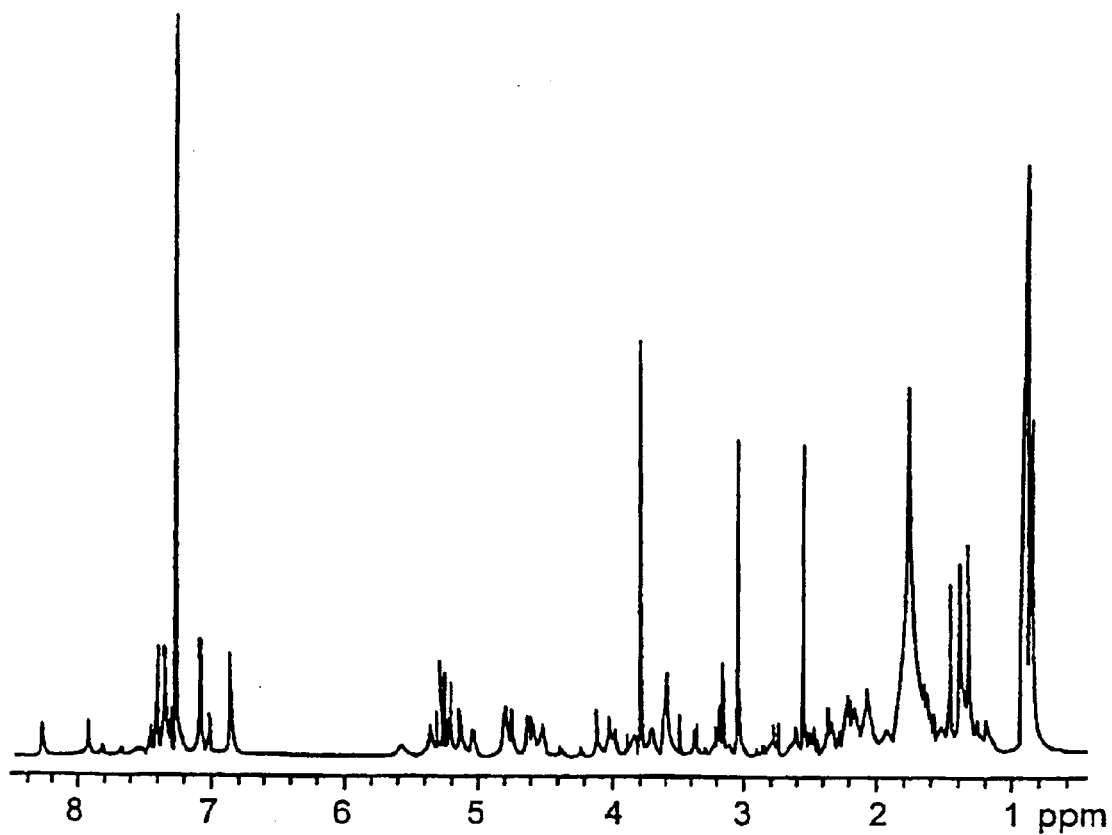
FIG. 20 is a $^1$H NMR spectrum of Benzyloxycarbonyldidemnin M (21).
Figure 21:
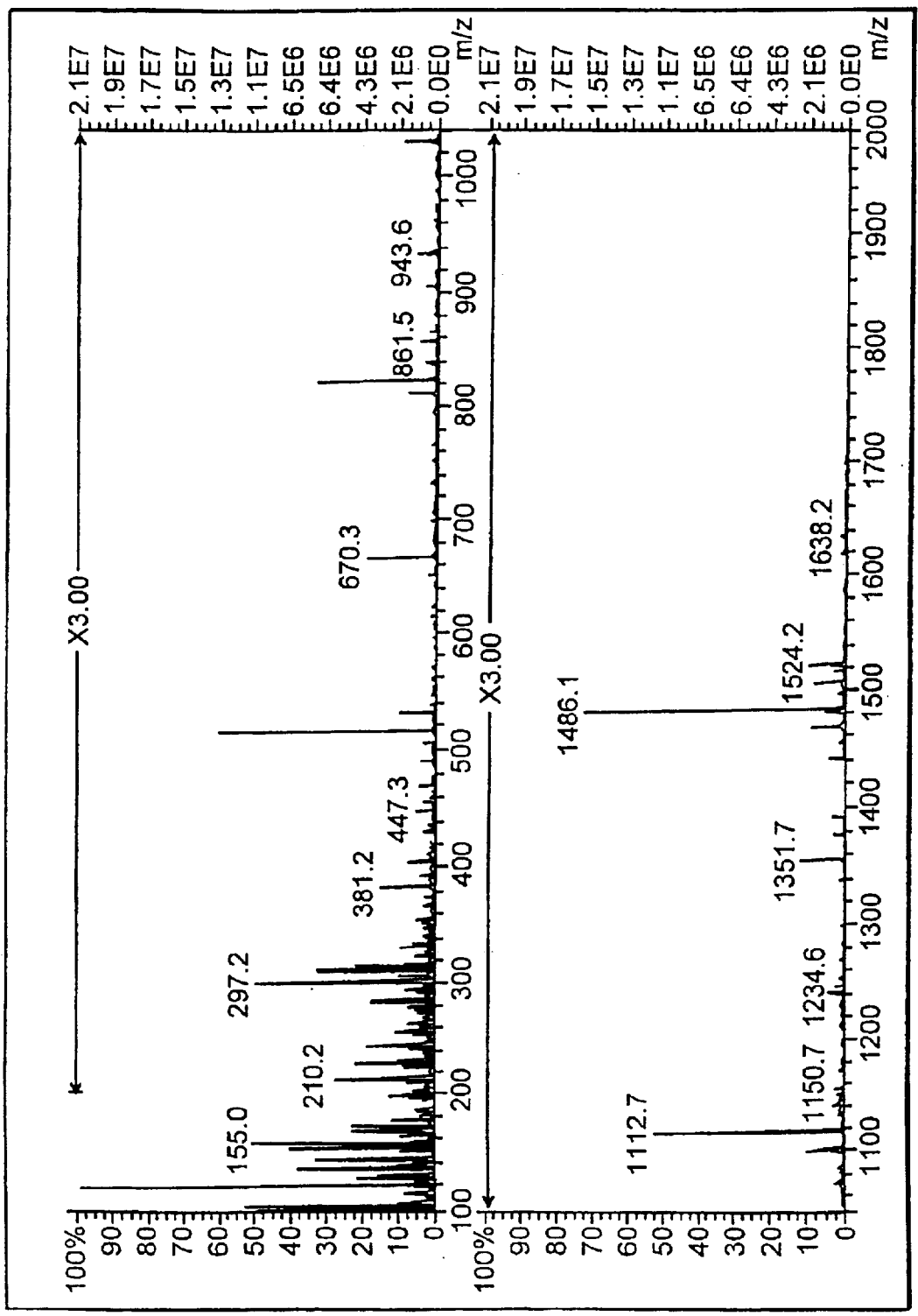
FIG. 21 is a LRFAB mass spectrum of Benzyloxycarbonyldidemnin M (21).
Figure 22:
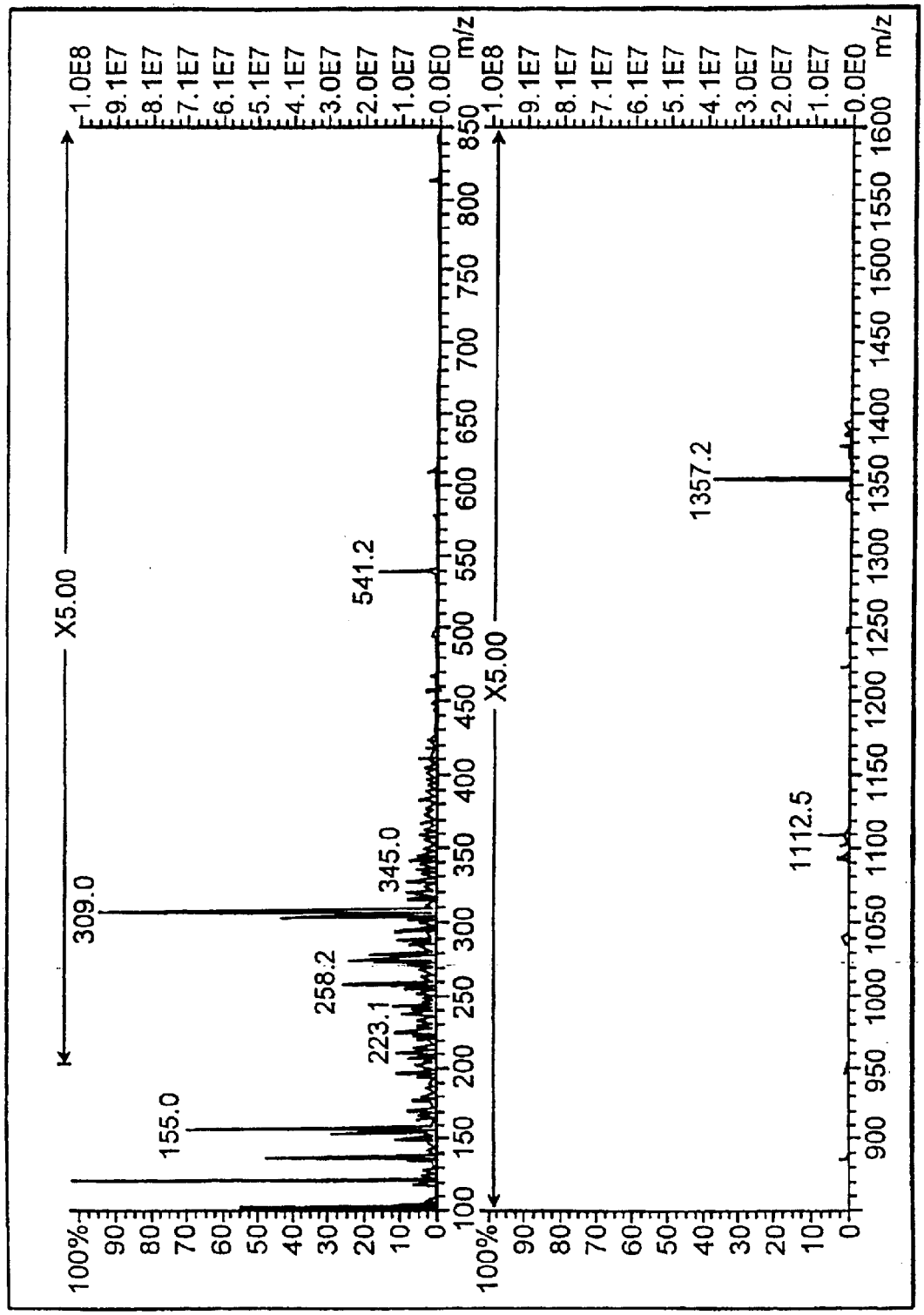
FIG. 22 is a LRFAB mass spectrum of Benzyloxycarbony-L-Pyroglutaminyldidemnin B (22).
Figure 23:
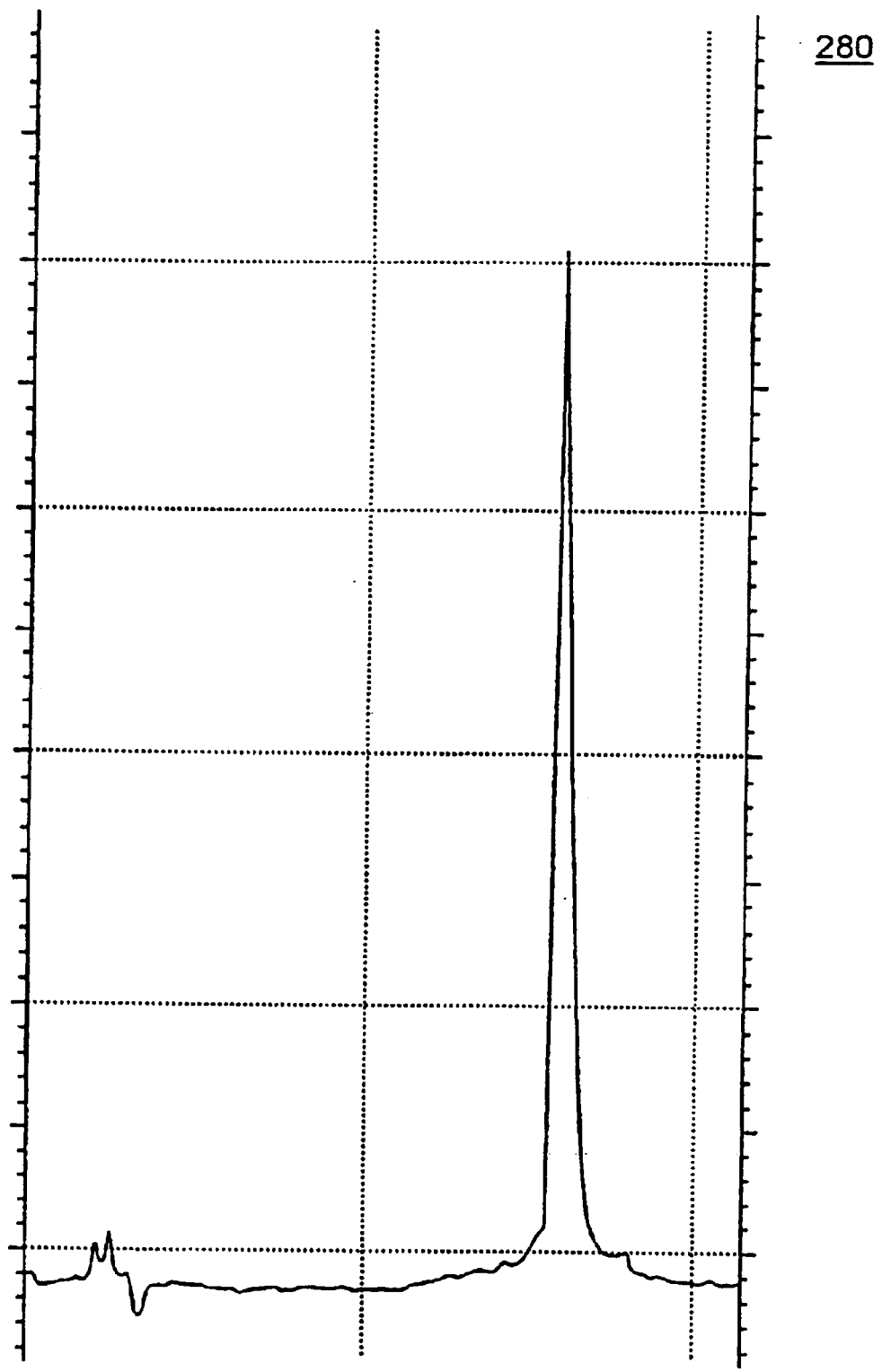
FIG. 23 is a RPHPLC trace of Pyroglutaminyldidemnin B (23).
Figure 24:
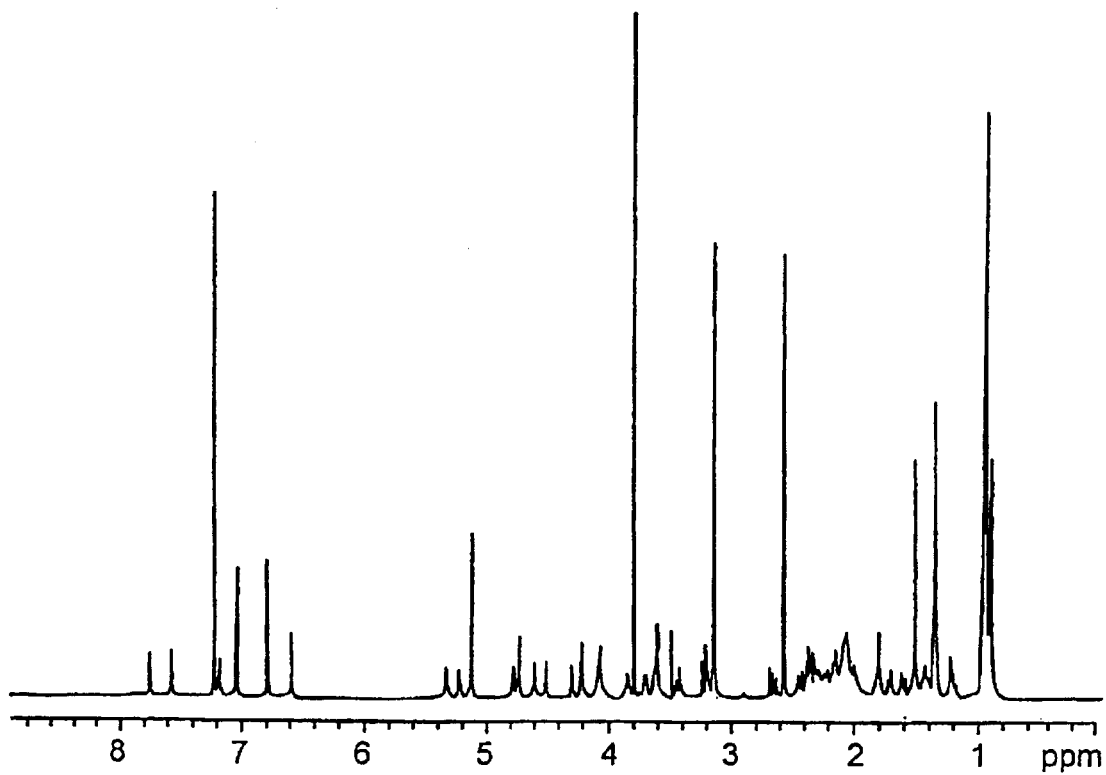
FIG. 24 is a $^1$H NMR spectrum of Pyroglutaminyldidemnin B (23).
Figure 25:
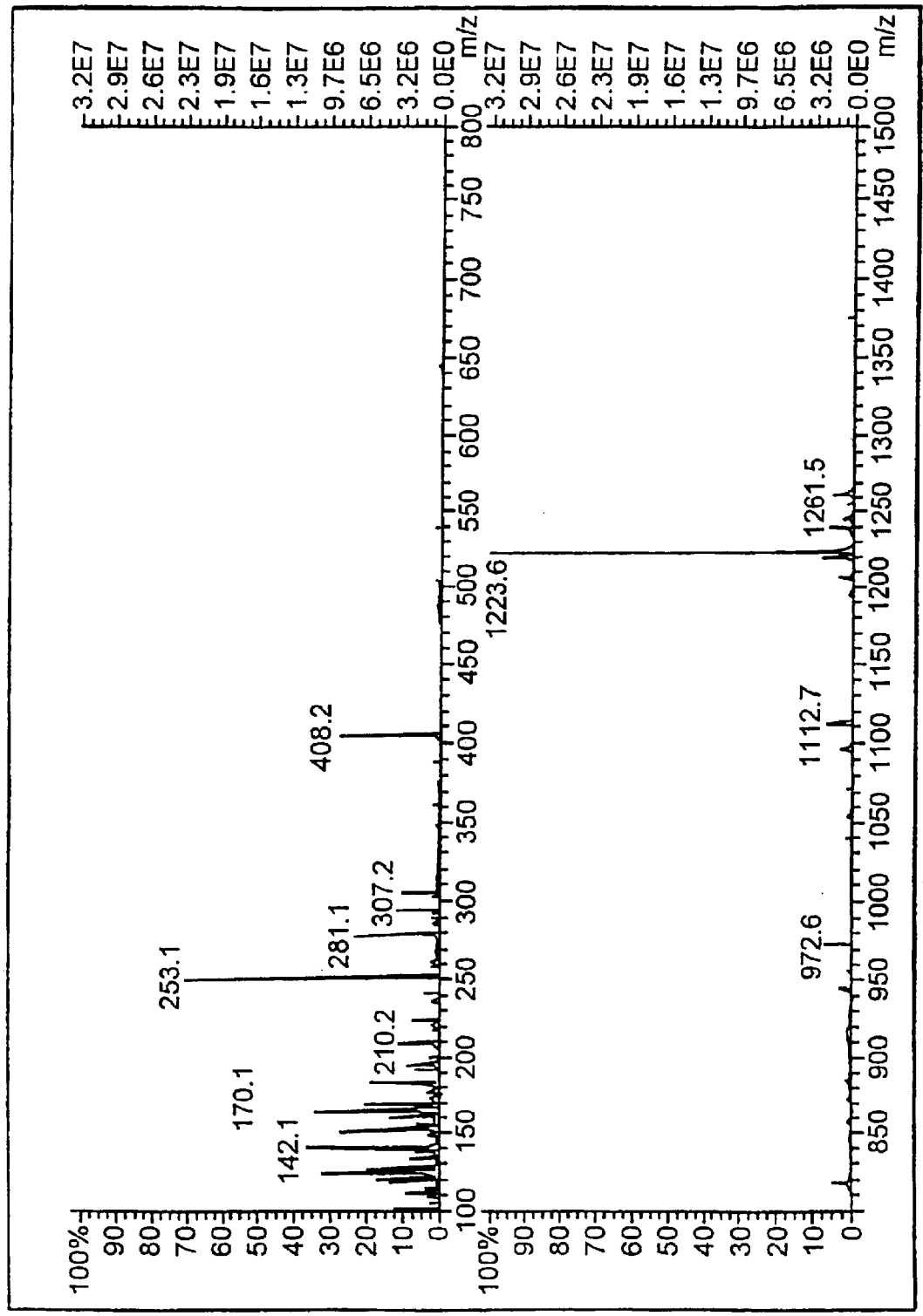
FIG. 25 is a LRFAB mass spectrum of Pyroglutaminyldidemnin B (23).
Figure 26:
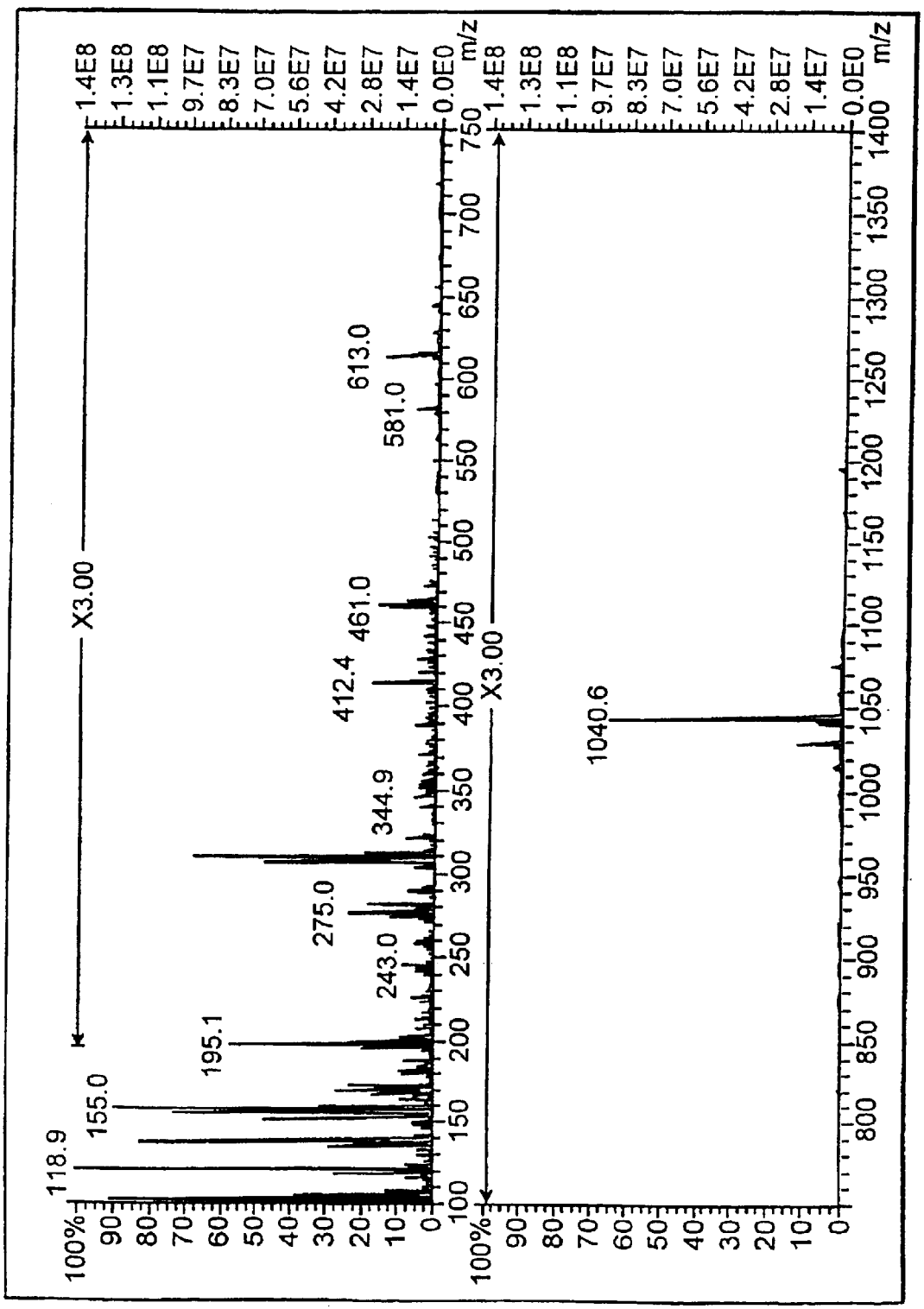
FIG. 26 is a LRFAB mass spectrum of Prolydidemnin A (25).
Figure 27:
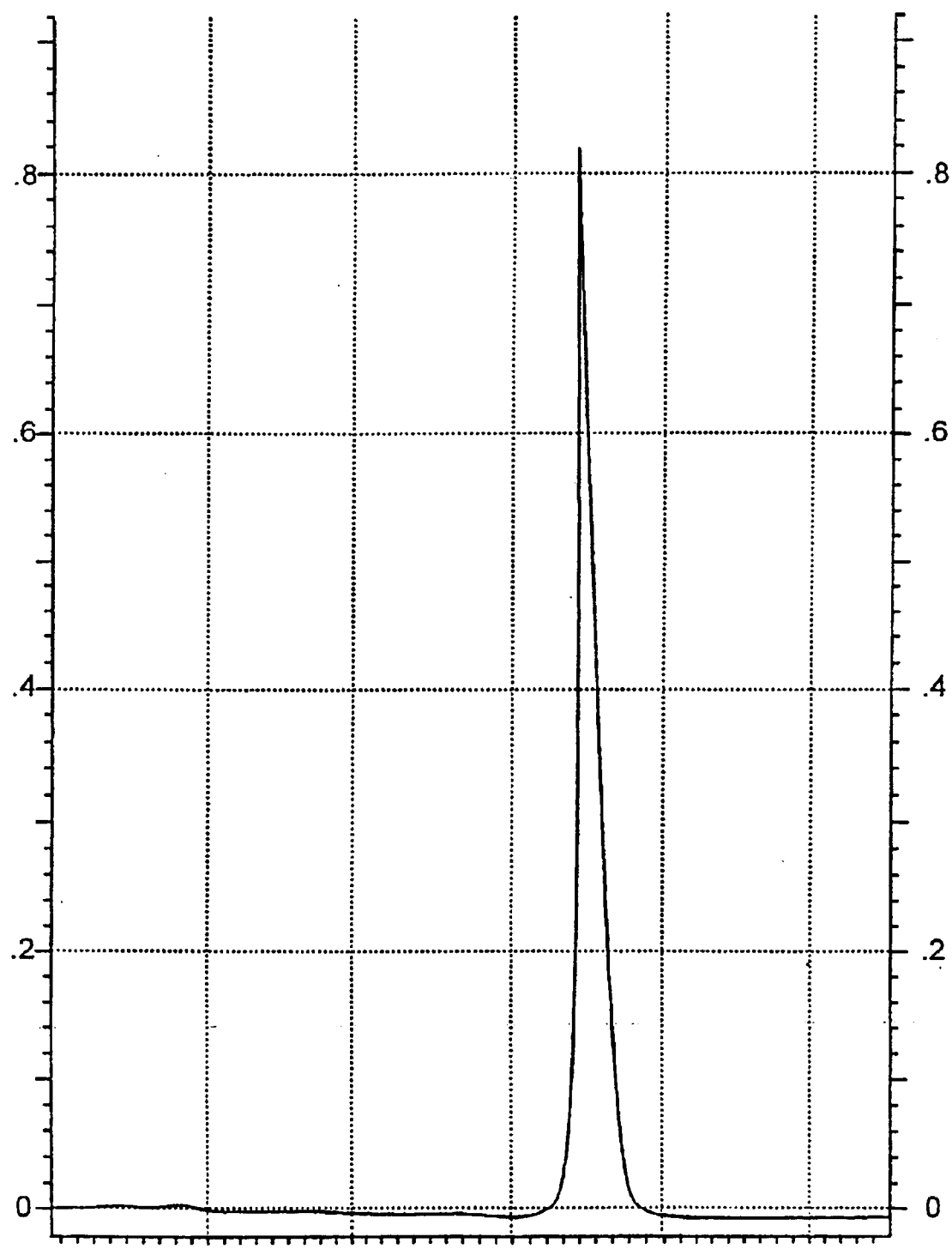
FIG. 27 is a RPHPLC trace of Dehydrodidemnin B.
Figure 28:
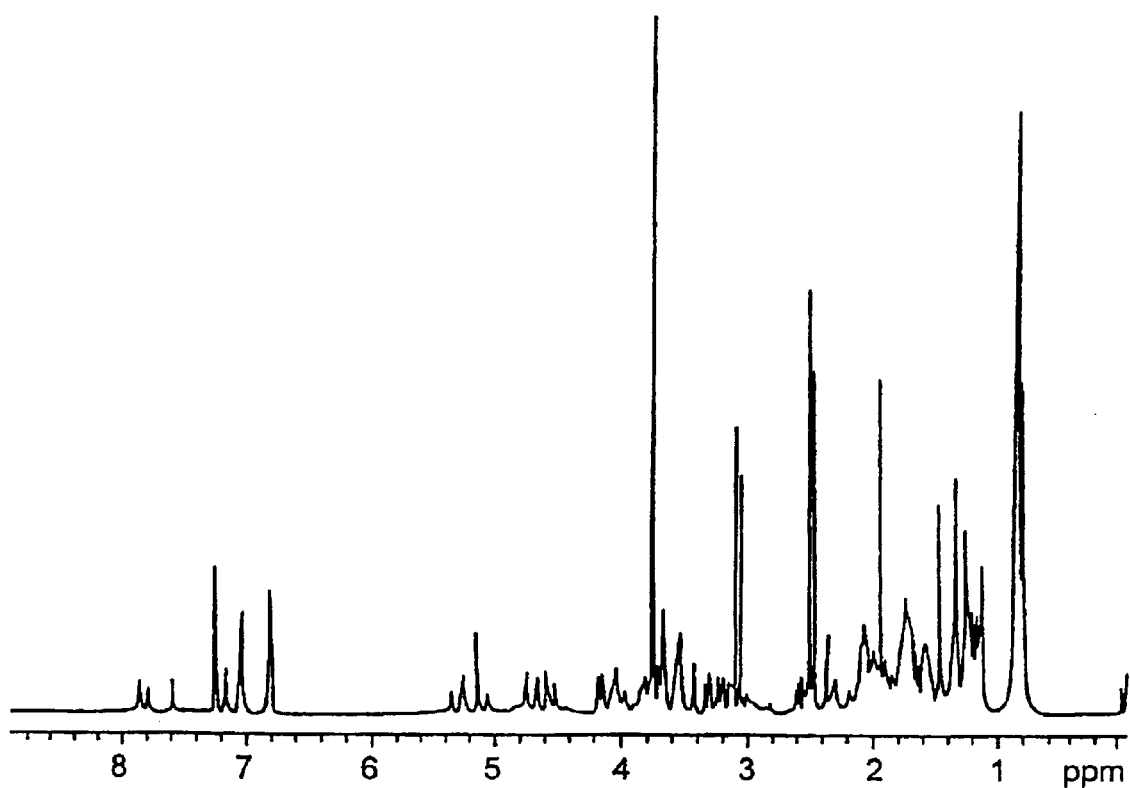
FIG. 28 is a $^1$H NMR spectrum of Dehydrodidemnin B.
Figure 29:
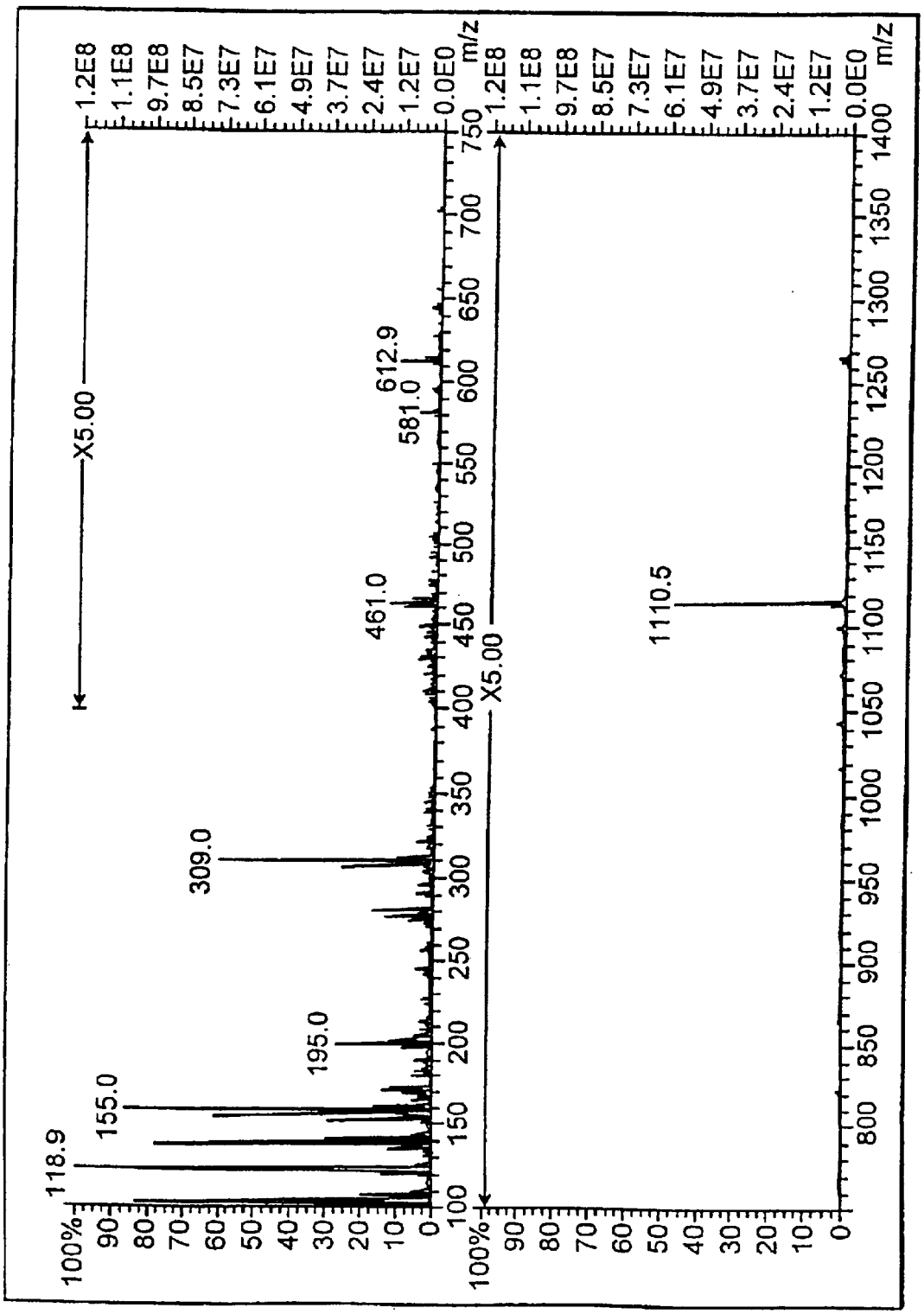
FIG. 29 is a LRFAB mass spectrum of Dehydrodidemnin B.

General Experimental Procedures. $^1$H NMR spectra were recorded on Varian XL-200, General Electric QE-300, Varian XL-400, and General Electric QN-500 spectrometers. $^1$H Chemical shifts are referenced in CDCl$_3$ and methanol-d$_4$ to residual CHCl$_3$ (7.26 ppm) and CD$_2$HOD (3.34 ppm). Electron impact (EI) mass spectra were recorded on a Finnigan MAT CH-5 DF spectrometer. High resolution (HRFAB) and fast atom bombardment (PAB) mass spectra were recorded on a VG ZAB-SE mass spectrometer operating in the FAB mode using magic bullet matrix.[27] Microanalytical results were obtained from the School of Chemical Sciences Microanalytical Laboratory. Infrared (IR) spectra were obtained on an IR/32 FTIR spectrophotometer. Solid samples were analyzed as chloroform solutions in sodium chloride cells. Liquids or oils were analyzed as neat films between sodium chloride plates.

Optical rotations (in degrees) were measured with a DIP 360 or a DIP 370 digital polarimeter with an Na lamp (589 nm) using a 5×0.35-cm (1.0 mL) cell. Melting points were determined on a capillary melting point apparatus and are not corrected. Normal phase column chromatography was performed using Merck-kieselgel silica gel (70–230 mesh). Fuji-Davison C18 gel (100–200 mesh) was used for reversed phase column chromatography. All solvents were spectral grade. Analytical thin layer chromatography was performed on precoated plates (Merck, F-254 indicator). These plates were developed by various methods including exposure to ninhydrin, iodine, and UV light (254 nm). HPLC was performed with a Waters 990 instrument and an Econosil C$_{18}$ column (Alltech/Applied Science) and a Phenomenex C$_{18}$ column.

THF was distilled from sodium benzophenone ketyl and CH$_2$Cl$_2$ from P$_2$O$_5$. Dimethylformamide (DMF), triethylamine (Et$_3$N), and N-methylmorpholine (NMM) were distilled from calcium hydride and stored over KOH pellets. Pyridine was distilled from KOH and stored over molecular sieves. Other solvents used in reactions were reagent grade without purification. Di-tert-butyl dicarbonate [(Boc)$_2$O], dicyclohexylcarbodiimide (DCC), 1-(3-dimethylaminopropyl)-3-ethylcarbodiimide hydrochloride (EDCI), dimethylaminopyridine (DMAP), 1-hydroxybenzotriazole (HOBT), L-glutamine, L-pyroglutamine, and L-proline were obtained from the Aldrich Chemical Company. All reactions requiring anhydrous conditions were performed under an atmosphere of nitrogen.

Pyroglutaminylglutamine (7). Pyroglutamic acid (0.11 g, 0.84 mmol) was dissolved in DMF (2.09 mL) and the solution was cooled to −20° C. N-Methylmorpholine (0.19 mL) and pivaloyl chloride (0.10 mL) were added to the solution and stirring continued at −20° C. for 5 h. At this time, a solution of glutamine t-butyl ester (0.20 g, 0.84 mmol) in DMF (0.42 mL) and N-methylmorpholine (92 mL) was added dropwise. Stirring was continued for 48 h, and the solution was allowed to warm to room temperature, then poured into H$_2$O and extracted with EtOAc. The EtOAc layer was washed with 1N HCl and H$_2$O, then dried (Na$_2$SO$_4$), and the solvent was carefully removed below 40° C. A white solid was isolated. Recrystallization from ether/petroleum ether provided 7 as a white crystalline material (0.17 g, 79%); FABMS 258.1 (M+H); HRFABMS calcd for C$_{10}$H$_{15}$N$_3$O$_5$ (M+H) 258.1090, found 258.1091.

Ethyl (S)-O-Benzyllactate (12). To a solution of ethyl (S)-lactate (2.36 g, 20.0 mmol) in THF (7.80 mL) was added sodium hydride (60% dispersion, 0.94 g, 24.0 mmol) portionwise, with cooling. Benzyl bromide (2.60 mL, 22.0 mmol) was then added via a dropping funnel. The reaction was allowed to stand at room temperature for 24 h. Ethyl acetate (70 mL) was slowly added to the reaction mixture, followed by water, to destroy the excess sodium hydride. The solution was then evaporated to dryness and the oily residue was partitioned between ether (30 mL) and water (60 mL). The ether layer was washed with aqueous sodium bicarbonate (5 mL) and brine. The solution was dried over sodium sulfate and the solvent evaporated to give an oily residue which crystallized overnight. Recrystallization of the crude product gave the compound as a white crystalline material (3.01 g, 72%); FABMS m/z 209.1 (M+H), 181.2 (M-C$_2$H$_4$).

O-Benzyllactic acid (13). To a cold solution of 12 (0.31 g, 1.49 mmol) in THF (14.9 mL) was added, dropwise, a cold 0.2 M lithium hydroxide solution (14.9 mL) during 10-min. Stirring continued for 3 h at ambient temperature, then the solution was concentrated to half its volume and washed with ether (2×15 mL). The combined ether layers were extracted with saturated NaHCO$_3$ (10 mL), and the aqueous layers were combined and acidified to pH 4 with 1 N potassium hydrogen sulfate. The acidified aqueous layer was extracted with ether (3×50 mL) and the combined ether extracts were dried (Na$_2$SO$_4$), filtered, and concentrated under reduced pressure, providing the corresponding acid an oil, which was used directly in the next step (0.21 g, 80%); $^1$H NMR (500 MHz, CDCl$_3$) δ1.46 (3H, d), 4.05 (1H, q), 4.55 (2H, dd), 7.31 (5H, s), 11.36 (1H, s); FABMS 219.0 (M+K), 203.1 (M+Na), 181.2 (M+H); HRFABMS calcd for C$_{10}$H$_{12}$NaO$_3$ (M+Na) 203.0684, found 203.0686; m/z calcd for C$_{10}$H$_{13}$O$_3$ (M+H) 181.0865, found 181.0864.

Boc-L-Proline Phenacyl Ester. Boc-proline (1.00 g, 4.65 mmol) was dissolved in ethyl acetate (29.4 mL), triethylamine (0.46 g, 0.63 mL) and phenacyl bromide (0.93 g, 4.68 mmol) were added and, within a few minutes, a precipitate formed. The mixture was stirred overnight, water and ether were added and the two layers separated. The organic layer was washed with 0.1N HCl, saturated sodium bicarbonate, and brine, then dried over MgSO$_4$. Evaporation of the solvent provided the desired compound (1.27 g, 83%); FABMS 334.2 (M+H), 234.1 (M+2H-Boc), 667.3 (2M+H); HRFABMS calcd for C$_{18}$H$_{23}$NO$_5$ (M+H) 334.1654, found 334.1665.

L-Proline phenacyl ester. Boc-L-proline phenacyl ester (0.29 g, 0.87 mmol) was dissolved in EtOAc (25 mL) and a steady current of HCl was passed through the solution for approximately 40 min, when TLC analysis showed the deprotection to be complete. The solvent was evaporated to provide a white crystalline material. Recrystallization from petroleum ether gave clear crystals (0.19 g, 94%); FABMS 234.2 (M+H), 467.2 (2M+H); HRFABMS calcd for C$_{13}$H$_{16}$NO$_3$ (M+H) 234.1130, found 234.1129.

L-O-Benzyllactyl-proline Phenacyl Ester (14). Proline phenacyl ester (0.19 g, 0.83 mmol) in CH$_2$Cl$_2$, DMAP (0.10 g, 0.83 mmol) and DCC (0.19 g, 0.96 mmol) were added at 0° C. to a solution of 13 (0.15 g, 0.83 mmol). The solution was allowed to warm to room temperature and stirred for 12 h. Dicyclohexylurea was filtered and washed with ethyl acetate. The filtrate and washings were combined and washed with 10% citric acid, 5% sodium bicarbonate and water, dried over MgSO$_4$ and concentrated. The crude residue was purified by flash chromatography eluting with hexane and ethyl acetate (4:1) to obtain the product (0.19 g, 57%) as an orange oil; FABMS 396.2 (M+H); HRFABMS calcd for C$_{23}$H$_{26}$NO$_5$ (M+H) 396.1811, found 396.1812.

L-O-Benzyllactyl-proline (8). Compound 14 (0.19 g, 0.48 mmol) was treated with Zn (0.96 g) in AcOH/H$_2$O (70:30), the mixture was allowed to stir at rt overnight, Zn was filtered off using celite, and the solution was partitioned between ether and water. The organic layer was separated and dried over Na$_2$SO$_4$ to afford the desired compound (0.11 g, 86%); FABMS 278.1 (M+H).

O-Benzyldidemnin B (15). L-O-Benzyllactyl-proline (33.0 mg, 0.13 mmol) in DMF (3 mL), DMAP (0.6 mg) and DCC (26.0 mg, 0.13 mmol) were added at 0° C. to a solution of didemnin A (39.7 mg, 0.42 mmol). The solution was allowed to warm to room temperature and stirred for 12 h, dicyclohexylurea was filtered and washed with ethyl acetate. The filtrate and washings were combined and washed with 10% citric acid, 5% sodium bicarbonate and water, and the extracts were dried over MgSO$_4$ and concentrated. The crude residue was purified by reversed phase HPLC using a gradient system of acetonitrile/H$_2$O to provide the compound as a yellow powder (40.5 mg, 80%); $^1$H NMR (500 MHz, CDCl$_3$), see Supplementary Material, S-1; FABMS 1241.2 (M+K), 1226.1 (M+Na), 1203.1 (M+H), see Supplementary Material, S-2; HRFABMS calcd for C$_{64}$H$_{96}$N$_7$O$_{15}$ (M+H) 1202.6964, found 1202.6964.

Didemnin B. Protected didemnin B (15, 40.5 mg, 33.7 mmol) was dissolved in isopropyl alcohol (5 mL), palladium on carbon (10%) catalyst (37.4 mg) was added and the solution was hydrogenated at room temperature and atmospheric pressure for 3 h, when TLC showed the reaction to be complete. The catalyst was filtered over celite and the solvent was evaporated to provide the desired compound as a white powder. Reversed phase HPLC (acetonitrile/H$_2$O gradient system) revealed the compound to be pure, see Supplementary Material, S-3 (32.1 mg, 86%); $^1$H NMR (500 MHz, CDCl$_3$), see Supplementary Material, S-4; FABMS 1134.5 (M+Na), 1112.5 (M+H), Supplementary Material, S-5; HRFABMS calcd for C$_{57}$H$_{90}$N$_7$O$_{15}$ (M+H) 1112.6495, found 1112.6491.

Pyroglutaminyl-glutaminyl-didemnin B [Didemnin M (1)]. Pyroglutaminylglutamine (3.42 mg, 14.4 μmol) was dissolved in DMF (36.0 μL) and the solution was cooled to −20° C. N-Methylmorpholine (3.27 μL) and pivaloyl chloride (1.72 μL) were added to the solution and stirring continued at −20° C. for 5 h, when a solution of didemnin B (16.0 mg, 14.4 μmol) in CH$_2$Cl$_2$ (7.23 μL) and N-methylmorpholine (1.59 μL) was added dropwise. Stirring continued for 48 h, then the solution was allowed to warm to room temperature, and the mixture was poured into H$_2$O and extracted with EtOAc. The EtOAc layer was washed with 1N HCl and H$_2$O, dried (Na$_2$SO$_4$), and solvent was carefully removed below 40° C. Reversed phase HPLC using a gradient system of acetonitrile/H$_2$O afforded the desired compound, see Supplementary Material, S-6 (8.1 mg, 79%); $^1$H NMR (500 MHz, CDCl$_3$), see Supplementary Material, S-7; FABMS m/z 1389.5 (M+K), 1374.5 (M+Na), 1351.6 (M+H), see Supplementary Material, S-8; HRFABMS m/z calcd for C$_{67}$H$_{103}$N$_{10}$O$_{19}$ (M+H) 1351.7401, found 1351.7406.

N-Benzyloxycarbonyl-L-glutamine (17). Glutamine (1.84 g, 12.62 mmol) was dissolved in 1 N NaOH (12.58 mL) and the solution was cooled to 0° C. and stirred for 30 min, when Na$_2$CO$_3$ (3.30 g) and benzyl chloroformate (4.38 mL) in dioxane (19.30 mL) were gradually added, in equal portions. Stirring continued at 0° C. for 1 h, then the solution was allowed to stir overnight at room temperature and was extracted with ethyl ether (2×20 mL). The aqueous solution was acidified with 2N HCl to pH 5 and extracted with ethyl acetate (3×50 mL), which was dried over sodium sulfate, and evaporated to give an oil which crystallized overnight. Recrystallization of the crude product gave a white crystalline material (3.07 g, 87%); FABMS 319.1 (M+K), 281.1 (M+H).

N-Benzyloxycarbonyl-L-glutaminyl-didemnin B (18). To a solution of Cbz-glutamine (0.14 g, 0.55 mmol) in dry DMF (2.50 mL), DMAP (0.6 mg) and DCC (20.6 mg, 0.11 mmol) were added at 20° C. with stirring. Stirring continued at room temperature for 2 h and a solution of didemnin B (23.0 mg, 20.6 μmol) in DMF (2.50 mL) was added with stirring. The solution was stirred at room temperature for 24 h, diluted with CH$_2$Cl$_2$ and washed with 5% NaHCO$_3$ and water to neutral pH. The solution was dried (Na$_2$SO$_4$) and evaporated to give a white solid which was purified by reversed phase HPLC using a gradient system of acetonitrile/water, see Supplementary Material, S-9 (51.3 mg, 34%); $^1$H NMR (500 MHz, CDCl$_3$), see Supplementary Material, S-10; FABMS 1374.6 (M+H), see Supplementary Material, S-11; HRFABMS calcd for C$_{70}$H$_{104}$N$_9$O$_{19}$ (M+H) 1374.7448, found 1374.7446. A second derivative was also obtained from HPLC purification (see Supplementary Material, S-12) and was found to be di-(benzyloxycarbonyl) glutaminyl-didemnin B (36.0 mg, 20%); $^1$H NMR (500 MHz, CDCl$_3$), see Supplementary Material, S-13, FABMS 1637.2 (M+H), see Supplementary Material, S-14; HRFABMS calcd for C$_{83}$H$_{118}$N$_{11}$O$_{23}$ (M+H) 1636.8402, found 1636.8401.

Glutaminyl-didemnin B (3). Compound 18 (25.1 mg, 18.2 μmol) was dissolved in isopropyl alcohol (1.00 mL) and 10% Pd/C catalyst (0.99 mg) was added. The solution was hydrogenated for 3 h. The catalyst was removed by filtration over celite and solvent was removed to afford 3 which was purified by reversed phase HPLC using a gradient system of acetonitrile/water (see Supplementary Material, S-15) (19.6 mg, 87%); $^1$H NMR (500 MHz, CDCl$_3$), see Supplementary Material, S-16; FABMS 1278.5 (M+K), 1262.6 (M+Na), 1240.7 (M+H), see Supplementary Material, S-17; HRFABMS calcd for C$_{62}$H$_{106}$N$_{11}$O$_9$ (M+H) 1240.7081, found 1240.7076.

Glutaminyl-glutaminyl-didemnin B (4). The procedure was identical to that described above for 3. Compound 4 was also prepared by treatment of 19 with hydrogen bromide in acetic acid; FABMS 1368.7 (M+H), see Supplementary Material, S-18; HRFABMS calcd for C$_{67}$H$_{106}$N$_{11}$O$_{19}$ (M+H) 1368.7666, found 1368.7680.

N-Benzyloxycarbonyl-L-pyroglutamine (20). L-Pyroglutamine (2.02 g, 13.83 mmol) was dissolved in 1 N NaOH (13.84 mL) and the solution was cooled to 0° C. After 30 min stirring, Na$_2$CO$_3$ (3.63 g) and benzyl chloroformate (4.82 mL) in dioxane (21.23 mL) were gradually added, in equal portions. Stirring was continued at 0° C. for 1 h, then the solution was stirred overnight at room temperature and extracted with ethyl ether (2×20 mL). The aqueous solution was acidified with 2N HCl to pH 5, extracted with ethyl acetate (3×50 mL), dried over sodium sulfate, and evaporated to give an oil which crystallized overnight. Recrystallization of the crude product gave white crystalline material (2.86 g, 87%); FABMS 240.1 (M+H).

L-(N-Benzyloxycarbonyl-pyroglutaminyl)-L-glutaminyl-didemnin B (21). To a solution of Cbz-pyroglutamine (10.2 mg, 38.7 µmol) in dry DMF (0.18 mL), DMAP (0.22 mg) and DCC (7.59 mg, 7.74 µmol) were added at 20° C. with stirring. Stirring continued at room temperature for 2 h and a solution of didemnin B (9.60 mg, 7.74 µmol) in DMF (2.50 mL) was added with stirring. The solution was stirred at room temperature for 24 h. The solution was diluted with $CH_2Cl_2$ and washed with 5% $NaHCO_3$ and water to neutral pH. The solution was dried ($Na_2SO_4$) and solvent evaporated to give 21 as a white solid. The compound was purified by reversed phase HPLC using a gradient system of acetonitrile/water (see Supplementary Material, S-19) (5.19 mg, 46%); $^1H$ NMR (500 MHz, $CDCl_3$), see Supplementary Material, S-20; FABMS 1524.2 (M+K), 1509.1 (M+Na), 1485.8 (M+H), see Supplementary Material, S-21; HRFABMS calcd for $C_{75}H_{109}N_{10}O_{21}$ (M+H) 1485.7769, found 1485.7765.

L-Pyroglutaminyl-L-glutaminyl-didemnin B [Didemnin M (1)]. Compound 21 (2.12 mg, 1.40 µmol) was dissolved in isopropyl alcohol (1.00 mL) and 10% Pd/C catalyst (9.90 µg) was added. The solution was hydrogenated for 3 h, catalyst was removed by filtration over celite and solvent was removed to afford the desired compound. The compound was purified by reversed phase HPLC using a gradient system of acetonitrile/water (see Supplementary Material, S-6) (1.66 mg, 88%); $^1H$ NMR (500 MHz, $CDCl_3$), see Supplementary Material, S-7; FABMS 1389.5 (M+K), 1374.5 (M+Na), 1351.6 (M+H), see Supplementary Material S-8; HRFABMS calcd for $C_{67}H_{103}N_{10}O_{19}$ (M+H) 1351.740.1, found 1351.7406.

N-Benzyloxycarbonyl-L-pyroglutaminyl-didemnin B (22). DMAP (0.48 mg) and EDC (16.5 mg, 88.0 µmol) were added at 20° C. with stirring to compound 20 (0.11 g, 0.44 mmol) in dry $CH_2Cl_2$ (2.00 mL). Stirring continued at room temperature for 2 h and a solution of didemnin B (9.20 mg, 8.24 µmol) in $CH_2Cl_2$ (2.00 mL) was added with stirring. The solution was stirred at room temperature for 24 h, diluted with $CH_2Cl_2$ and washed with 5% $NaHCO_3$ and water to neutral pH. The solution was dried ($Na_2SO_4$) and the solvent evaporated to give the compound as a white solid. The compound was purified by reversed phase HPLC using a gradient system of acetonitrile/water (5.70 mg, 52%); FABMS 1356.7 (M+H), see Supplementary Material, S-22; HRFABMS calcd for $C_{70}H_{102}N_9O_{18}$ (M+H) 1356.7343, found 1356.7335.

L-Pyroglutaminyl-didemnin B (2). Compound 22 (5.70 mg, 4.28 µmol) was dissolved in isopropyl alcohol (0.5 mL) and 10% Pd/C catalyst (0.25 mg) was added. The solution was hydrogenated for 5 h, catalyst was removed by filtration, and the solvent was removed to afford 22, which was purified by reversed phase HPLC using a gradient system of acetonitrile/water, see Supplementary Material, S-23 (4.28 mg, 82%); $^1H$ NMR (500 MHz, $CDCl_3$), see Supplementary Material, S-24; FABMS 1223.7 (M+H), see Supplementary Material, S-25; HRFABMS calcd for $C_{62}H_{95}N_8O_{17}$ (M+H) 1223.6815, found 1223.6811.

Boc-L-prolyl-didemnin A (24). DMAP (0.75 mg) and EDC (11.5 mg, 60.0 mmol) were added at 20° C. with stirring to Boc-L-proline (23) (25.0 mg, 0.12 mmol) in dry $CH_2Cl_2$ (2.00 mL). Stirring continued at room temperature for 2 h and a solution of didemnin B (44.4 mg, 40.0 mmol) in $CH_2Cl_2$ (2.00 mL) was added with stirring. The solution was stirred at room temperature for 24 h. The solution was diluted with $CH_2Cl_2$ and washed with 5% $NaHCO_3$ solution and water to neutral pH. The solution was dried ($Na_2SO_4$) and the solvent evaporated to give the compound as a white solid (17.5 mg, 42%); FABMS 1140.6. (M+H), 1040.6 (M+2H-Boc).

L-Prolyl-didemnin B (25). Compound 24 (15.1 mg, 13.2 µmol) was dissolved in 5N HCl in ethyl acetate. After 3 h stirring at room temperature, TLC analysis showed the deprotection to be complete. The solvent was evaporated to provide a white crystalline material (12.5 mg, 91%); FABMS 1040.6 (M+H), see Supplementary Material, S-26.

Dehydrodidemnin B. DMAP (0.16 mg) and DCC (2.62 mg, 12.8 µmol) were added at 20° C. with stirring to a solution of pyruvic acid (2.61 mg, 29.7 µmol) in dry DMF (0.10 mL). Stirring continued at room temperature for 2 h and a solution of prolyl-didemnin A (10.3 mg, 9.90 µmol) in DMF (0.40 mL) was added with stirring. The solution was stirred at room temperature for 24 h, diluted with $CH_2Cl_2$ and washed with 5% $NaHCO_3$ solution and water to neutral pH, then dried ($Na_2SO_4$) and the solvent evaporated to give the product as a white solid. The compound was purified by reversed phase HPLC using a gradient system of acetonitrile/water (see Supplementary Material, S-27) to give a white powdery substance; $^1H$ NMR (500 MHz, $CDCl_3$), see Supplementary Material, S-28; FABMS 1110.6 (M+H), see Supplementary Material, S-29; HRFABMS calcd for $C_{57}H_{88}N_7O_{15}$ (M+H) 1110.6338, found 1110.6334.

TABLE I

Antiviral Activities of Didemnins[a] (# - New Compounds)

| | Compound | ng/mL | HSV/CV-1 Cytotoxocity[b] | Activity[c] |
|---|---|---|---|---|
| # | Gln-Didemnin B | 100 | 16 | ? |
| | | 50 | 16 | ? |
| | | 20 | 16 | ? |
| | | 10 | 0 | +++ |
| # | Cbz-Gln-Didemnin B (161) | 100 | 0 | + |
| | | 50 | 0 | + |
| | | 20 | 0 | + |
| | | 10 | 0 | − |
| | Didemnin M (5) | 100 | 16 | ? |
| | | 50 | 16 | ? |
| | | 20 | 0 | +++ |
| | | 10 | 0 | + |
| # | pGlu-Didemnin B (39) | 100 | 16 | ? |
| | | 50 | 16 | ? |
| | | 20 | 0 | +++ |
| | | 10 | 0 | + |
| # | Cbz-pGlu-Didemnin B (145) | 100 | 0 | + |
| | | 50 | 0 | + |
| | | 20 | 0 | + |
| | | 10 | 0 | − |
| # | Gln[GlnIst$^2$]-Didemnin B (160) | 100 | 0 | +++ |
| | | 50 | 0 | + |
| | | 20 | 0 | + |
| | | 10 | 0 | + |
| # | Cbz-Gln[Cbz-GlnIst$^2$]DB (162) | 100 | 0 | +++ |
| | | 50 | 0 | + |
| | | 20 | 0 | + |
| | | 10 | 0 | + |
| | O-Bu-Didemnin B (140) | 100 | 16 | ? |
| | | 50 | 9 | + |
| | | 20 | 8 | + |
| | | 10 | 0 | + |
| | Didemnin (B) (2) | 100 | 16 | ? |
| | | 50 | 0 | +++ |
| | | 20 | 0 | +++ |
| | | 10 | 0 | + |
| | Dehydrodidemnin B (6) | 100 | 16 | ? |
| | | 50 | 16 | ? |
| | | 20 | 0 | +++ |
| | | 10 | 0 | + |
| | Didemnin A (1) | 100 | 0 | + |
| | | 50 | 0 | + |

TABLE I-continued

Antiviral Activities of Didemnins[a] (# - New Compounds)

| Compound | HSV/CV-1 | | |
|---|---|---|---|
| | ng/mL | Cytotoxocity[b] | Activity[c] |
| | 20 | 0 | + |
| | 10 | 0 | − |

FOOTNOTES:
[a]Performed by Dr. G. R. Wilson in this laboratory;
[b]0 (least toxic) to 16 (toxic);
[c]+++ = complete inhibition; ++ = strong inhibition; + = moderate inhibition; − = no inhibition.

TABLE III

T/C (% of Control, Life Extension) vs. P388

| | Murine Leukemia in Mice | |
|---|---|---|
| | T/C | Dose, mg/kg |
| #Gln-DB | 185 | 1 |
| | 171 | 0.05 |
| | 152 | 0.025 |

TABLE II

Cytotoxicity of Didemnins[a] # = New Compounds

| | Dose (ng/mL) | | | | |
|---|---|---|---|---|---|
| | 250 | 25 | 2.5 | 0.25 | IC$_{50}$ |
| Compounds | Inhibition (%) | | | | (ng/mL) |
| # Gln-Didemnin B (141) | 100 | 100 | 100 | 94 | 0.1 |
| # PGlu-Didemnin B (39) | 100 | 100 | 100 | 94 | 0.1 |
| Dehydrodidemnin B (6) | 100 | 100 | 100 | 95 | 0.2 |
| Didemnin M (6) | 100 | 100 | 100 | 94 | 0.8 |
| Didemnin B (2) | 100 | 100 | 40 | 0 | 7 |
| O-Bu-didemlnin B (140) | 100 | 97 | 0 | NT[b] | 10 |
| Prolyl-didemnin A (43) | 100 | 99 | 40 | 30 | 12 |
| # Cbz-Gln-didemnin B (161) | 100 | 87 | 0 | 0 | 25 |
| # (Cbz-Gln)$_2$-didemnin B (162) | 99 | 87 | 0 | 0 | 50 |
| # (Gln)$_2$-didemnin B (160) | 100 | 87 | 0 | 0 | 50 |
| # Cbz-pGlu-didemnin B (145) | 100 | 70 | 0 | 0 | 50 |
| Didemnin A (1) | 100 | 70 | 0 | 0 | 75 |
| Boc-Pro-didemnin A (158) | 100 | 55 | 0 | 0 | 85 |

[a]Performed by Dr. G. R. Wilson in this laboratory.
[b]NT = not tested.

TABLE III

T/C (% of Control, Life Extension) vs. P388

| | Murine Leukemia in Mice | |
|---|---|---|
| | T/C | Dose, mg/Kg |
| #Gln-DB | 185 | 1 |
| | 171 | 0.05 |
| | 152 | 0.025 |

What is claimed is:

1. Glutaminyl didemnin derivatives having the following structure:

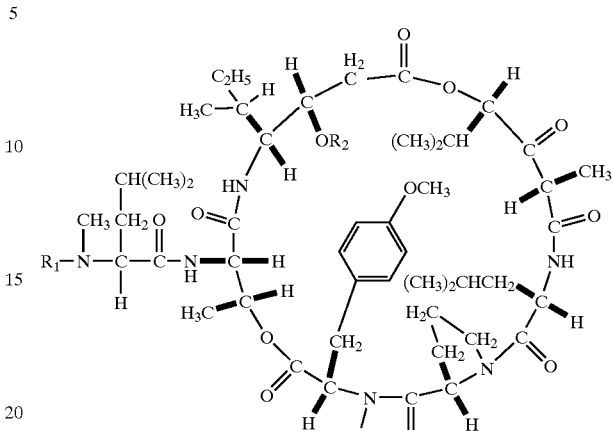

wherein $R_1$ and $R_2$ are selected in accordance with the following table:

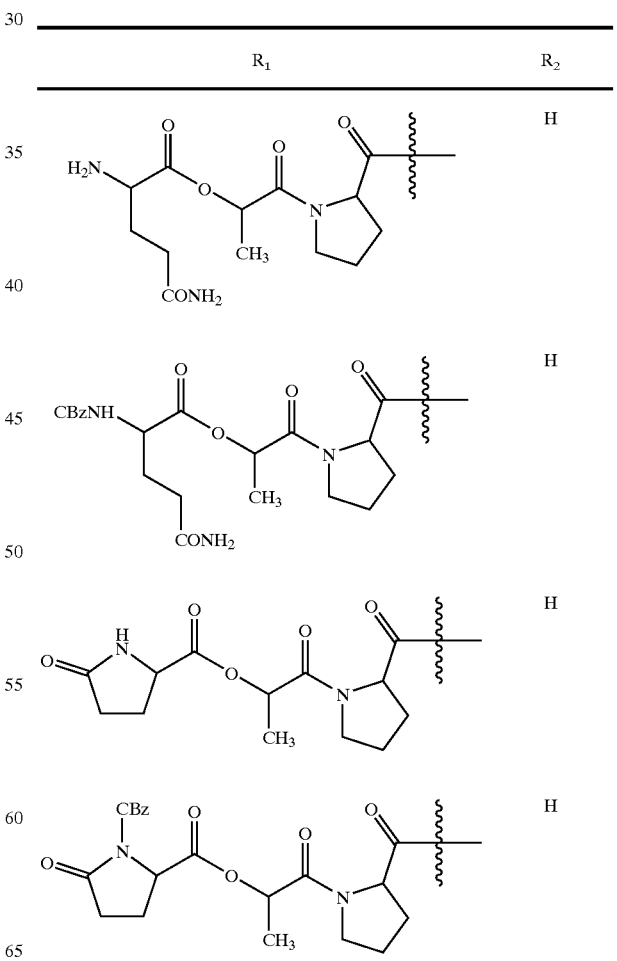

-continued

| R₁ | R₂ | |
|---|---|---|
| 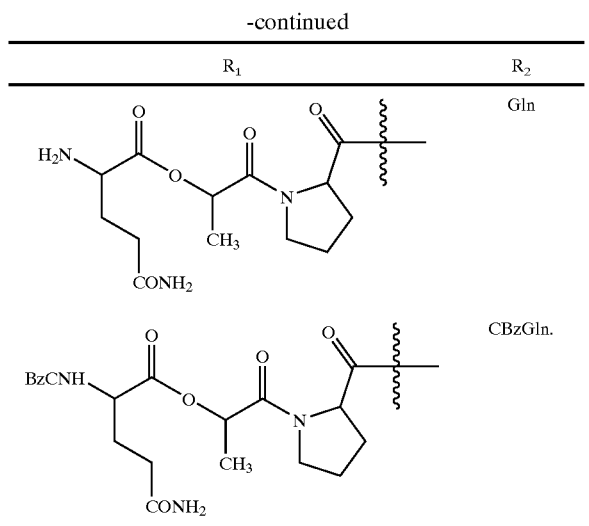 | Gln | |
| | CBzGln. | |

2. The glutaminyl didemnin derivative of claim 1, known as Gln-Didemnin B, having the following formula (3):

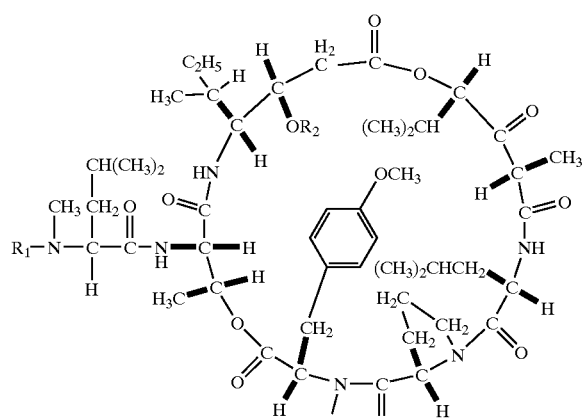

wherein R₁ is

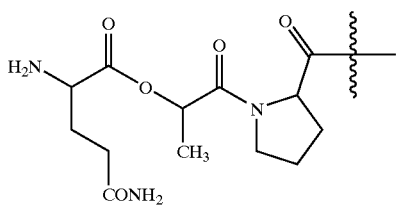

and R₂ is H.

3. A pharmaceutical composition comprising the compound Gln-Didemnin B and an optional pharmaceutically acceptable excipient, diluent or carrier.

4. The glutaminyl didemnin derivative of claim 1, know as Cbz-Gln-Didemnin B, having the following formula (18):

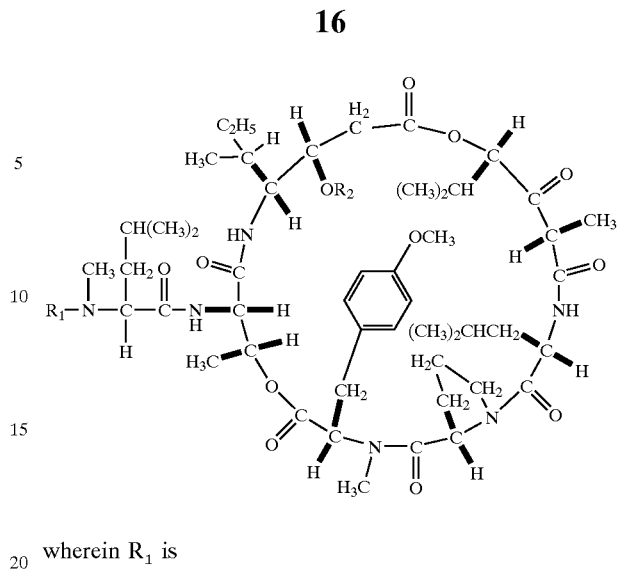

wherein R₁ is and R₂ is H.

5. A pharmaceutical composition comprising the compound Cbz-Gln-Didemnin B and an optional pharmaceutically acceptable excipient, diluent or carrier.

6. The glutaminyl didemnin derivative of claim 1, known as pGlu-Didemnin B, having the following formula (2):

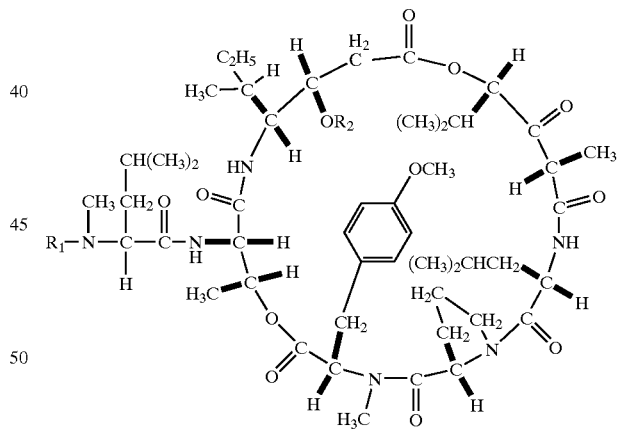

wherein R₁ is and R₂ is H.

7. A pharmaceutical composition comprising the compound pGlu-Didemnin B and an optional pharmaceutically excipient, diluent or carrier.

8. The glutaminyl didemnin derivative of claim 1, known as Cbz-pGlu-Didemnin B, having the following formula (22):

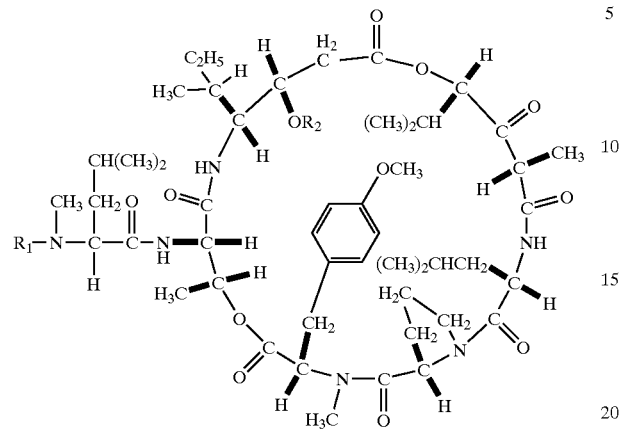

wherein $R_1$ is

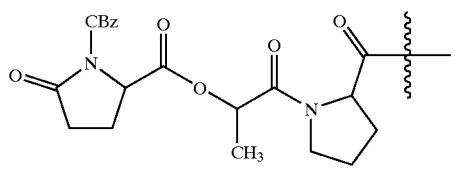

and $R_2$ is H.

9. A pharmaceutical composition comprising the compound Cbz-pGlu-Didemnin B and an optional pharmaecutially acceptable excipient, diluent or carrier.

10. The glutaminyl didemnin derivative of claim 1, known as Gln[Gln1st$^2$]-Didemnin B, having the following formula (4):

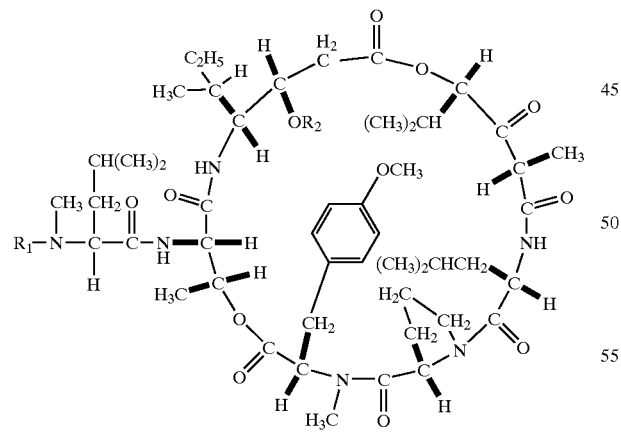

wherein $R_1$ is

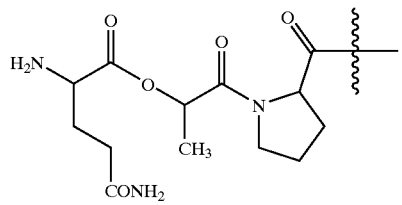

and $R_2$ is Gln.

11. A pharmaceutical comprising the compound Gln [Gln1st$^2$]-Didemnin B and an optional pharmaceutically acceptable excipient, diluent or carrier.

12. The glutaminyl didemnin derivative of claim 1, know as Cbz-Gln[Cbz-Gln1st$^2$]-Didemnin B, having the following formula (19):

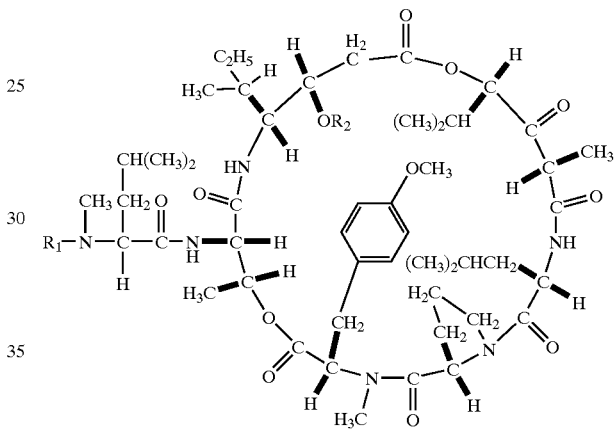

wherein $R_1$ is

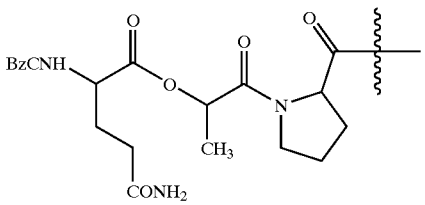

and $R_2$ is CBzGln.

13. A pharmaceutical composition comprising the compound Cbz-Gln[Cbz-Gln1st$^2$]-Didemnin B and an optional pharmaceutically acceptable excipient, diluent or carrier.

* * * * *